US012797480B2

(12) United States Patent
Hua et al.

(10) Patent No.: US 12,797,480 B2
(45) Date of Patent: Nov. 17, 2026

(54) ANTIBODY-DRUG CONJUGATE AND MEDICAL USE THEREOF

(71) Applicants: Shanghai Hansoh Biomedical Co., Ltd., Shanghai (CN); Jiangsu Hansoh Pharmaceutical Group Co., Ltd., Lianyungang (CN)

(72) Inventors: Haiqing Hua, Shanghai (CN); Dongjie Mao, Shanghai (CN); Yan Luo, Shanghai (CN); Yuejun Xie, Shanghai (CN)

(73) Assignees: Shanghai Hansoh Biomedical Co., Ltd., Shanghai (CN); Jiangsu Hansoh Pharmaceutical Group Co., Ltd., Lianyungang (CN)

( * ) Notice: Subject to any disclaimer, the term of this patent is extended or adjusted under 35 U.S.C. 154(b) by 630 days.

(21) Appl. No.: 18/263,091

(22) PCT Filed: Jan. 26, 2022

(86) PCT No.: PCT/CN2022/073943

§ 371 (c)(1),
(2) Date: Jul. 26, 2023

(87) PCT Pub. No.: WO2022/161385

PCT Pub. Date: Aug. 4, 2022

(65) Prior Publication Data

US 2024/0165252 A1 May 23, 2024

(30) Foreign Application Priority Data

Jan. 29, 2021 (CN) ........................ 202110123809.3

(51) Int. Cl.

| | |
|---|---|
| ***A61K 47/68*** | (2017.01) |
| ***A61K 39/00*** | (2006.01) |
| ***A61P 35/00*** | (2006.01) |
| ***C07D 491/22*** | (2006.01) |
| ***C07K 16/28*** | (2006.01) |

(52) U.S. Cl.

CPC ........ *A61K 47/68037* (2023.08); *A61K 39/00* (2013.01); *A61K 47/6849* (2017.08); *A61P 35/00* (2018.01); *C07D 491/22* (2013.01); *C07K 16/2878* (2013.01)

(58) Field of Classification Search

CPC ............ A61K 47/6807; A61K 47/6849; A61K 47/549; A61K 47/60; A61K 39/44; A61K 47/545; A61P 35/00

See application file for complete search history.

(56) References Cited

U.S. PATENT DOCUMENTS

2017/0252458 A1* 9/2017 Albone .............. A61K 47/6803

FOREIGN PATENT DOCUMENTS

| | | | | | |
|---|---|---|---|---|---|
| CN | 109265550 | A | | 1/2019 | |
| CN | 109293772 | A | | 2/2019 | |
| CN | 111689980 | A | * | 9/2020 | ......... A61K 47/6835 |
| CN | 112028996 | A | | 12/2020 | |
| WO | 2020063673 | A1 | | 4/2020 | |
| WO | WO-2020063676 | A1 | * | 4/2020 | .............. A61P 35/02 |
| WO | 2020244657 | A1 | | 12/2020 | |
| WO | WO-2021018168 | A1 | * | 2/2021 | ........... G01N 33/575 |

OTHER PUBLICATIONS

Cho S-F et al. Targeting B Cell Maturation Antigen (BCMA) in Multiple Myeloma: Potential Uses of BCMA-Based Immunotherapy. (Front Immunol 2018 9:1821 1-15. doi: 10.3389/fimmu.2018.01821) (Year: 2018).*
Translated WO 2020/063676 (Year: 2020).*
Translated WO 2021/018168 (Year: 2021).*
Translated CN 111689980 A (Year: 2020).*
Talele TT et al. The "Cyclopropyl Fragment" is a Versatile Player that Frequently Appears in Preclinical/Clinical Drug Molecules (J. Med. Chem. 2016, 59, 19, 8712-8756) (Year: 2016).*
Written Opinion of the International Searching Authority; China National Intellectual Property Administration; International Application No. PCT/CN2022/073943; mailed Apr. 28, 2022; 10 pages.
International Preliminary Report on Patentability; The International Bureau of WIPO; International Application No. PCT/CN2022/073943; issued Jul. 31, 2023; 6 pages.
IUPAC-IUB Commission on Biochemical Nomenclature, A One-Letter Notation for Amino Acid Sequences, Tentative Rules, Journal of Biological Chemistry, 1968, vol. 243, No. 13, pp. 3557-3559.
Holliger et al., "Engineered antibody fragments and the rise of single domains," Nature Biotechnology, 2005, vol. 23, No. 9, pp. 1126-1136.
Harlow et al., "Antibodies: A Laboratory Manual," Cold Spring Harbor Laboratory, 1988, Chapters 5-8 and 15.
International Search Report; China National Intellectual Property Administration; International Application No. PCT/CN2022/073943; Apr. 28, 2022; 3 pages.

* cited by examiner

*Primary Examiner* — Karen A. Canella
*Assistant Examiner* — John J Skoko, III
(74) *Attorney, Agent, or Firm* — Taft Stettinius & Hollister LLP

(57) ABSTRACT

An anti-BCMA antibody-drug conjugate, or a pharmaceutically acceptable salt or solvent compound thereof, and the medical use thereof. Specifically, the antibody-drug conjugate is formed by connecting an anti-BCMA antibody or an antigen-binding fragment thereof and an exatecan derivative by using a linker, and the antibody-drug conjugate or the pharmaceutically acceptable salt or solvent compound thereof has a significant anti-tumor effect and good safety.

15 Claims, No Drawings

Specification includes a Sequence Listing.

SEQUENCE LISTING

```
<160> NUMBER OF SEQ ID NOS: 23

<210> SEQ ID NO 1
<211> LENGTH: 121
<212> TYPE: PRT
<213> ORGANISM: Artificial Sequence
<220> FEATURE:
<223> OTHER INFORMATION: Heavy chain variable region of murine mab M1

<400> SEQUENCE: 1

Gln Val Gln Leu Gln Gln Ser Gly Ala Glu Leu Val Arg Pro Gly Ala
1               5                   10                  15

Ser Val Lys Leu Ser Cys Lys Ala Leu Gly Tyr Ser Phe Ser Asp Tyr
            20                  25                  30

Glu Met His Trp Val Arg Gln Thr Pro Val His Gly Leu Glu Trp Ile
        35                  40                  45

Gly Gly Ile His Pro Gly Ser Gly Gly Ser Ala Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Leu Asp Tyr Gly Tyr Ser Trp Ala Trp Phe Pro Tyr Trp Gly
            100                 105                 110

Gln Gly Thr Leu Val Thr Val Ser Ala
        115                 120


<210> SEQ ID NO 2
<211> LENGTH: 106
<212> TYPE: PRT
<213> ORGANISM: Artificial Sequence
<220> FEATURE:
<223> OTHER INFORMATION: Light chain variable domain of murine mab M1

<400> SEQUENCE: 2

Glu Ile Leu Leu Thr Gln Ser Pro Ala Ile Ile Val Thr Ser Pro Gly
1               5                   10                  15

Glu Lys Val Thr Ile Thr Cys Ser Ala Ser Ser Ser Val Ile Tyr Met
            20                  25                  30

Asn Trp Tyr Gln Gln Lys Pro Gly Ser Ser Pro Lys Ile Trp Ile Tyr
        35                  40                  45

Gly Ile Ser Asn Leu Ala Ser Gly Val Pro Ala Arg Phe Ser Gly Ser
    50                  55                  60

Gly Ser Gly Thr Ser Phe Ser Phe Thr Ile Asn Ser Met Glu Ala Glu
```

-continued

```
65                  70                  75                  80

Asp Val Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105


<210> SEQ ID NO 3
<211> LENGTH: 10
<212> TYPE: PRT
<213> ORGANISM: Artificial Sequence
<220> FEATURE:
<223> OTHER INFORMATION: HCDR1 of murine mab M1

<400> SEQUENCE: 3

Gly Tyr Ser Phe Ser Asp Tyr Glu Met His
1               5                   10


<210> SEQ ID NO 4
<211> LENGTH: 17
<212> TYPE: PRT
<213> ORGANISM: Artificial Sequence
<220> FEATURE:
<223> OTHER INFORMATION: HCDR2 of murine mab M1

<400> SEQUENCE: 4

Gly Ile His Pro Gly Ser Gly Gly Ser Ala Tyr Asn Gln Lys Phe Lys
1               5                   10                  15

Gly


<210> SEQ ID NO 5
<211> LENGTH: 14
<212> TYPE: PRT
<213> ORGANISM: Artificial Sequence
<220> FEATURE:
<223> OTHER INFORMATION: HCDR3 of murine mab M1

<400> SEQUENCE: 5

Thr Arg Leu Asp Tyr Gly Tyr Ser Trp Ala Trp Phe Pro Tyr
1               5                   10


<210> SEQ ID NO 6
<211> LENGTH: 10
<212> TYPE: PRT
<213> ORGANISM: Artificial Sequence
<220> FEATURE:
<223> OTHER INFORMATION: LCDR1 of murine mab M1

<400> SEQUENCE: 6

Ser Ala Ser Ser Ser Val Ile Tyr Met Asn
1               5                   10


<210> SEQ ID NO 7
<211> LENGTH: 7
<212> TYPE: PRT
<213> ORGANISM: Artificial Sequence
<220> FEATURE:
<223> OTHER INFORMATION: LCDR2 of murine mab M1

<400> SEQUENCE: 7

Gly Ile Ser Asn Leu Ala Ser
1               5


<210> SEQ ID NO 8
<211> LENGTH: 9
<212> TYPE: PRT
```

<213> ORGANISM: Artificial Sequence
<220> FEATURE:
<223> OTHER INFORMATION: LCDR3 of murine mab M1

<400> SEQUENCE: 8

Gln Gln Arg Ser Ser Tyr Pro Leu Thr
1 5

<210> SEQ ID NO 9
<211> LENGTH: 121
<212> TYPE: PRT
<213> ORGANISM: Artificial Sequence
<220> FEATURE:
<223> OTHER INFORMATION: Humanized heavy chain variable region HCVR1

<400> SEQUENCE: 9

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Ser Asp Tyr
20 25 30

Glu Met His Trp Val Arg Gln Ala Pro Gly Gln Gly Leu Glu Trp Met
35 40 45

Gly Gly Ile His Pro Gly Ser Gly Gly Ser Ala Tyr Asn Gln Lys Phe
50 55 60

Lys Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Thr Arg Leu Asp Tyr Gly Tyr Ser Trp Ala Trp Phe Pro Tyr Trp Gly
100 105 110

Gln Gly Thr Leu Val Thr Val Ser Ala
115 120

<210> SEQ ID NO 10
<211> LENGTH: 121
<212> TYPE: PRT
<213> ORGANISM: Artificial Sequence
<220> FEATURE:
<223> OTHER INFORMATION: Humanized heavy chain variable region HCVR2

<400> SEQUENCE: 10

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Ser Asp Tyr
20 25 30

Glu Met His Trp Val Arg Gln Ala Pro Gly Gln Gly Leu Glu Trp Ile
35 40 45

Gly Gly Ile His Pro Gly Ser Gly Gly Ser Ala Tyr Asn Gln Lys Phe
50 55 60

Lys Gly Arg Val Thr Leu Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Leu Asp Tyr Gly Tyr Ser Trp Ala Trp Phe Pro Tyr Trp Gly
100 105 110

Gln Gly Thr Leu Val Thr Val Ser Ala
115 120

<210> SEQ ID NO 11

<211> LENGTH: 121
<212> TYPE: PRT
<213> ORGANISM: Artificial Sequence
<220> FEATURE:
<223> OTHER INFORMATION: Humanized heavy chain variable region HCVR3

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Asp Tyr
            20                  25                  30

Glu Met His Trp Val Arg Gln Ala Pro Gly Gln Gly Leu Glu Trp Ile
        35                  40                  45

Gly Gly Ile His Pro Gly Ser Gly Gly Ser Ala Tyr Asn Gln Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Asp Tyr Gly Tyr Ser Trp Ala Trp Phe Pro Tyr Trp Gly
            100                 105                 110

Gln Gly Thr Leu Val Thr Val Ser Ala
        115                 120
```

<210> SEQ ID NO 12
<211> LENGTH: 106
<212> TYPE: PRT
<213> ORGANISM: Artificial Sequence
<220> FEATURE:
<223> OTHER INFORMATION: Humanized light chain variable region LCVR1

<400> SEQUENCE: 12

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ile Tyr Met
            20                  25                  30

Asn Trp Tyr Gln Gln Lys Pro Gly Gln Ala Pro Arg Leu Leu Ile Tyr
        35                  40                  45

Gly Ile Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gly Gly Thr Lys Val Glu Ile Lys
            100                 105
```

<210> SEQ ID NO 13
<211> LENGTH: 106
<212> TYPE: PRT
<213> ORGANISM: Artificial Sequence
<220> FEATURE:
<223> OTHER INFORMATION: Humanized light chain variable region LCVR2

<400> SEQUENCE: 13

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ile Tyr Met
            20                  25                  30
```

```
Asn Trp Tyr Gln Gln Lys Pro Gly Gln Ser Pro Lys Ile Trp Ile Tyr
        35                  40                  45

Gly Ile Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gly Gly Thr Lys Val Glu Ile Lys
            100                 105


<210> SEQ ID NO 14
<211> LENGTH: 106
<212> TYPE: PRT
<213> ORGANISM: Artificial Sequence
<220> FEATURE:
<223> OTHER INFORMATION: Humanized light chain variable region LCVR3

<400> SEQUENCE: 14

Glu Ile Leu Leu Thr Gln Ser Pro Ala Thr Leu Ser Leu Ser Pro Gly
1               5                   10                  15

Glu Arg Ala Thr Leu Thr Cys Ser Ala Ser Ser Ser Val Ile Tyr Met
            20                  25                  30

Asn Trp Tyr Gln Gln Lys Pro Gly Ser Ser Pro Lys Ile Trp Ile Tyr
        35                  40                  45

Gly Ile Ser Asn Leu Ala Ser Gly Val Pro Ala Arg Phe Ser Gly Ser
    50                  55                  60

Gly Ser Gly Thr Ser Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gly Gly Thr Lys Val Glu Ile Lys
            100                 105


<210> SEQ ID NO 15
<211> LENGTH: 451
<212> TYPE: PRT
<213> ORGANISM: Artificial Sequence
<220> FEATURE:
<223> OTHER INFORMATION: Ab1 HC

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Asp Tyr
            20                  25                  30

Glu Met His Trp Val Arg Gln Ala Pro Gly Gln Gly Leu Glu Trp Met
        35                  40                  45

Gly Gly Ile His Pro Gly Ser Gly Gly Ser Ala Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Leu Asp Tyr Gly Tyr Ser Trp Ala Trp Phe Pro Tyr Trp Gly
            100                 105                 110

Gln Gly Thr Leu Val Thr Val Ser Ala Ala Ser Thr Lys Gly Pro Ser
        115                 120                 125
```

-continued

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 16
<211> LENGTH: 451
<212> TYPE: PRT
<213> ORGANISM: Artificial Sequence
<220> FEATURE:
<223> OTHER INFORMATION: Ab2 HC

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Asp Tyr
            20                  25                  30
```

-continued

```
Glu Met His Trp Val Arg Gln Ala Pro Gly Gln Gly Leu Glu Trp Ile
        35                  40                  45

Gly Gly Ile His Pro Gly Ser Gly Gly Ser Ala Tyr Asn Gln Lys Phe
    50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Asp Tyr Gly Tyr Ser Trp Ala Trp Phe Pro Tyr Trp Gly
            100                 105                 110

Gln Gly Thr Leu Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445
```

-continued

```
Pro Gly Lys
    450


<210> SEQ ID NO 17
<211> LENGTH: 451
<212> TYPE: PRT
<213> ORGANISM: Artificial Sequence
<220> FEATURE:
<223> OTHER INFORMATION: Ab3 HC

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Asp Tyr
            20                  25                  30

Glu Met His Trp Val Arg Gln Ala Pro Gly Gln Gly Leu Glu Trp Ile
        35                  40                  45

Gly Gly Ile His Pro Gly Ser Gly Gly Ser Ala Tyr Asn Gln Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Asp Tyr Gly Tyr Ser Trp Ala Trp Phe Pro Tyr Trp Gly
            100                 105                 110

Gln Gly Thr Leu Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

-continued

```
Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 18
<211> LENGTH: 213
<212> TYPE: PRT
<213> ORGANISM: Artificial Sequence
<220> FEATURE:
<223> OTHER INFORMATION: Ab1 LC

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ile Tyr Met
            20                  25                  30

Asn Trp Tyr Gln Gln Lys Pro Gly Gln Ala Pro Arg Leu Leu Ile Tyr
        35                  40                  45

Gly Ile Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 19
<211> LENGTH: 213
<212> TYPE: PRT
<213> ORGANISM: Artificial Sequence
<220> FEATURE:
```

<223> OTHER INFORMATION: Ab2 LC

<400> SEQUENCE: 19

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ile Tyr Met
            20                  25                  30

Asn Trp Tyr Gln Gln Lys Pro Gly Gln Ser Pro Lys Ile Trp Ile Tyr
        35                  40                  45

Gly Ile Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 20
<211> LENGTH: 213
<212> TYPE: PRT
<213> ORGANISM: Artificial Sequence
<220> FEATURE:
<223> OTHER INFORMATION: Ab3 LC

<400> SEQUENCE: 20

```
Glu Ile Leu Leu Thr Gln Ser Pro Ala Thr Leu Ser Leu Ser Pro Gly
1               5                   10                  15

Glu Arg Ala Thr Leu Thr Cys Ser Ala Ser Ser Ser Val Ile Tyr Met
            20                  25                  30

Asn Trp Tyr Gln Gln Lys Pro Gly Ser Ser Pro Lys Ile Trp Ile Tyr
        35                  40                  45

Gly Ile Ser Asn Leu Ala Ser Gly Val Pro Ala Arg Phe Ser Gly Ser
    50                  55                  60

Gly Ser Gly Thr Ser Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 21
<211> LENGTH: 65
<212> TYPE: PRT
<213> ORGANISM: Artificial Sequence
<220> FEATURE:
<223> OTHER INFORMATION: His-tagged human BCMA extracellular region

<400> SEQUENCE: 21

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala His His His His His His His His His His
    50                  55                  60

His
65


<210> SEQ ID NO 22
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

-continued

```
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 23
<211> LENGTH: 107
<212> TYPE: PRT
<213> ORGANISM: Artificial Sequence
<220> FEATURE:
<223> OTHER INFORMATION: Light chain constant region

<400> SEQUENCE: 23

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

ANTIBODY-DRUG CONJUGATE AND MEDICAL USE THEREOF

CROSS-REFERENCE TO RELATED APPLICATIONS

The present application is a U.S. National Stage application of International Application No. PCT/US2022/073943 filed on Jan. 26, 2022, which claims the priority of the Chinese patent application No. 202110123809.3 filed on Jan. 29, 2021. The contents of each of those applications are incorporated herein by reference in their entireties.

SEQUENCE LISTING

This application incorporates by reference the material in the ASCII text file titled CHENG-46_ST25.txt, which was created on Jul. 27, 2023 and is 32 KB.

FIELD OF THE INVENTION

The present disclosure relates to the field of biomedicine and specifically the present disclosure relates to an anti-BCMA antibody drug conjugate and medical use thereof.

BACKGROUND OF THE INVENTION

B cells are lymphocytes, which play an important role in adaptive humoral immunity and the production of antibodies that specifically recognize antigens. The three subtypes of B cells are naive B cells, memory B cells and plasma cells. In the process of VDJ recombination, two or three fragments of DNA selected from a genomic library are recombined to produce a combinatorial array of antibody variable domains, thereby at most $10^9$ unique B cell lineages are generated by further altering the variable domains encoded by B cells of different lineages, resulting in antibodies specific for unique targets. B cells are involved in many diseases. Malignant transformation of B cells lead to cancer, including some lymphomas, such as multiple myeloma and Hodgkin's lymphoma. B cells are also involved in autoimmune diseases, including systemic lupus erythematosus (SLE) and IgA nephropathy. B cell-related cancers and autoimmune diseases can be considered as abnormality of B cell function, thus a possible strategy to control such diseases is to use antibodies that target pathological B cells.

BCMA is a member of the TNF receptor superfamily, which is a non-glycosylated intrinsic membrane receptor for the ligands BAFF (a B-cell activator) and APRIL (a proliferation-inducing ligand). BCMA and its corresponding ligands can regulate different functions of humoral immunity, B cell development and homeostasis. BCMA is expressed by tonsillar memory B cells and germinal center B cells, it is detected in the spleen, lymph node, thymus, adrenal gland and liver, and a variety of analysis of B cell lineages show that the expression level of BCMA increases after maturation.

SUMMARY OF THE INVENTION

The objective of the present disclosure is to provide an antibody-drug conjugate of general formula (I) or a pharmaceutically acceptable salt or solvate thereof, (I)

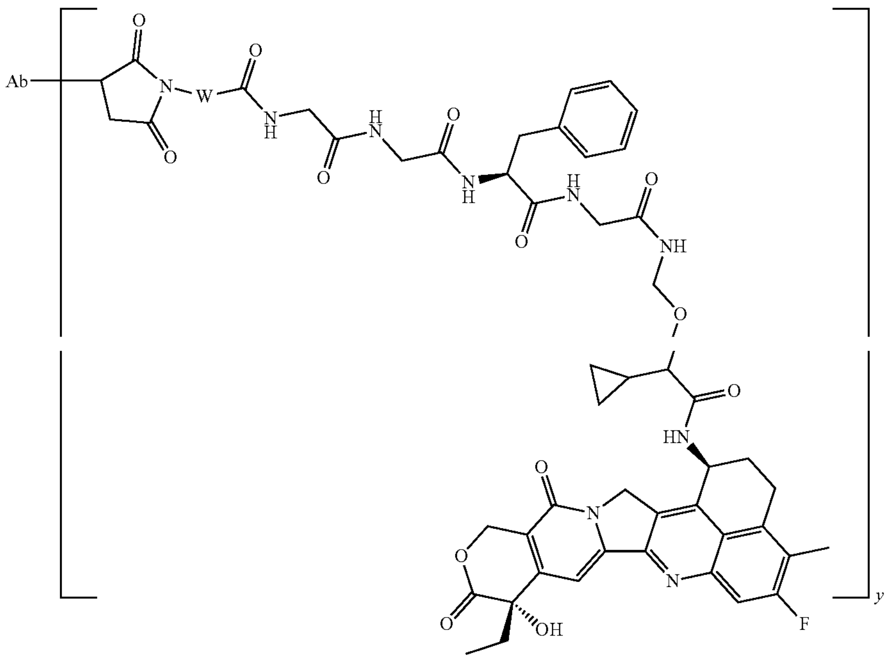

wherein:

W is $-(CR^eR^f)_g-X_1-(CR^eR^f)_u-X_2-(CR^eR^f)_h-$;

$R^e$ or $R^f$ is independently selected from the group consisting of hydrogen, deuterium, hydroxyl, amino, alkyl, halogen, haloalkyl, deuterated alkyl, hydroxyalkyl; preferably, $R^e$ or $R^f$ is independently selected from the group consisting of hydrogen, deuterium; more preferably, $R^e$ or $R^f$ is hydrogen;

$X_1$ or $X_2$ is independently selected from the group consisting of N, H, O and S; preferably, $X_1$ or $X_2$ is independently selected from S; more preferably, $X_1$ or $X_2$ is independently selected from O;

g, u or h is independently selected from the group consisting of 1, 2, 3 and 4; preferably, g, u or h is independently selected from 1, 2, 3; more preferably, g, u or h is 2;

y is 1-20; preferably, y is 4-10; more preferably, y is 4, 6, 8 or 10;

Ab is an anti-BCMA antibody or an antigen-binding fragment thereof.

In a preferred embodiment of the present disclosure, the anti-BCMA antibody or the antigen-binding fragment thereof comprises a heavy chain variable region and a light chain variable region, wherein the heavy chain variable region comprises an HCDR1, an HCDR2 and an HCDR3 set forth in SEQ ID NO: 3, SEQ ID NO: 4 and SEQ ID NO: 5, respectively, and the light chain variable region comprises an LCDR1, an LCDR2 and an LCDR3 set forth in SEQ ID NO: 6, SEQ ID NO: 7 and SEQ ID NO: 8, respectively.

In a preferred embodiment of the present disclosure, the anti-BCMA antibody or the antigen-binding fragment thereof is a marine antibody, a chimeric antibody, a human antibody, or a humanized antibody.

In a preferred embodiment of the present disclosure, the anti-BCMA antibody or the antigen-binding fragment thereof further comprises a heavy chain constant region derived from human IgG1, IgG2, IgG3 or IgG4 or variant thereof;

Preferably, the anti-BCMA antibody or the antigen-binding fragment thereof further comprises a heavy chain constant region derived from human IgG1, IgG2, or IgG4;

More preferably, the anti-BCMA antibody or the antigen-binding fragment thereof further comprises IgG1 heavy chain constant region with enhanced ADCC toxicity after amino acid mutation; alternatively, the anti-BCMA antibody or the antigen-binding fragment thereof further comprises heavy chain constant region as shown in SEQ ID NO: 22.

In a preferred embodiment of the present disclosure, the anti-BCMA antibody or the antigen-binding fragment thereof further comprises a light chain constant region derived from human κ chain, λ chain or variant thereof; preferably, the anti-BCMA antibody or the antigen-binding fragment thereof further comprises a light chain constant region derived from human κ chain; more preferably, the anti-BCMA antibody or the antigen-binding fragment thereof further comprises a light chain constant region as shown in SEQ ID NO: 23.

In a preferred embodiment of the present disclosure, the anti-BCMA antibody or the antigen-binding fragment thereof comprises a heavy chain variable region selected from the group consisting of SEQ ID NO: 9, SEQ ID NO: 10 and SEQ ID NO: 11, or a heavy chain variable region having at least 70%, 75%, 80%, 85%, 90%, 95% or 99% identity with the same;

and/or the anti-BCMA antibody or the antigen-binding fragment thereof comprises a light chain variable region selected from the group consisting of SEQ ID NO: 12, SEQ ID NO: 13 and SEQ ID NO: 14, or a light chain variable region having at least 70%, 75%, 80%, 85%, 90%, 95% or 99% identity with the same.

In a preferred embodiment of the present disclosure, the anti-BCMA antibody or the antigen-binding fragment thereof comprises a heavy chain selected from the group consisting of SEQ ID NO: 15, SEQ ID NO: 16 and SEQ ID NO: 17, or a heavy chain having at least 80%, 85%, 90%, 95% or 99% identity with the same.

and/or the anti-BCMA antibody or the antigen-binding fragment thereof comprises a light chain selected from the group consisting of SEQ ID NO: 18, SEQ ID NO: 19 and SEQ ID NO: 20, or a light chain having at least 80%, 85%, 90%, 95% or 99% identity with the same.

In a preferred embodiment of the present disclosure, the anti-BCMA antibody or the antigen-binding fragment thereof comprises a heavy chain variable region as shown in SEQ ID NO: 9 and a light chain variable region as shown in SEQ ID NO: 12; or the anti-BCMA antibody or the antigen-binding fragment thereof comprises a heavy chain variable region as shown in SEQ ID NO: 10 and a light chain variable region as shown in SEQ ID NO: 13; or the anti-BCMA antibody or the antigen-binding fragment thereof comprises a heavy chain variable region as shown in SEQ ID NO: 11 and a light chain variable region as shown in SEQ ID NO: 14.

In a preferred embodiment of the present disclosure, the anti-BCMA antibody comprises a heavy chain as shown in SEQ ID NO: 15 and a light chain as shown in SEQ ID NO: 18, or the anti-BCMA antibody comprises a heavy chain as shown in SEQ ID NO: 16 and a light chain as shown in SEQ ID NO: 19, or the anti-BCMA antibody comprises a heavy chain as shown in SEQ ID NO: 17 and a light chain as shown in SEQ ID NO: 20.

In a preferred embodiment of the present disclosure, the antibody drug conjugate or the pharmaceutically acceptable salt or solvate thereof is as shown in general formula (II), or a tautomer, mesomer, racemate, enantiomer, diastereomer or mixture form thereof;

(II)

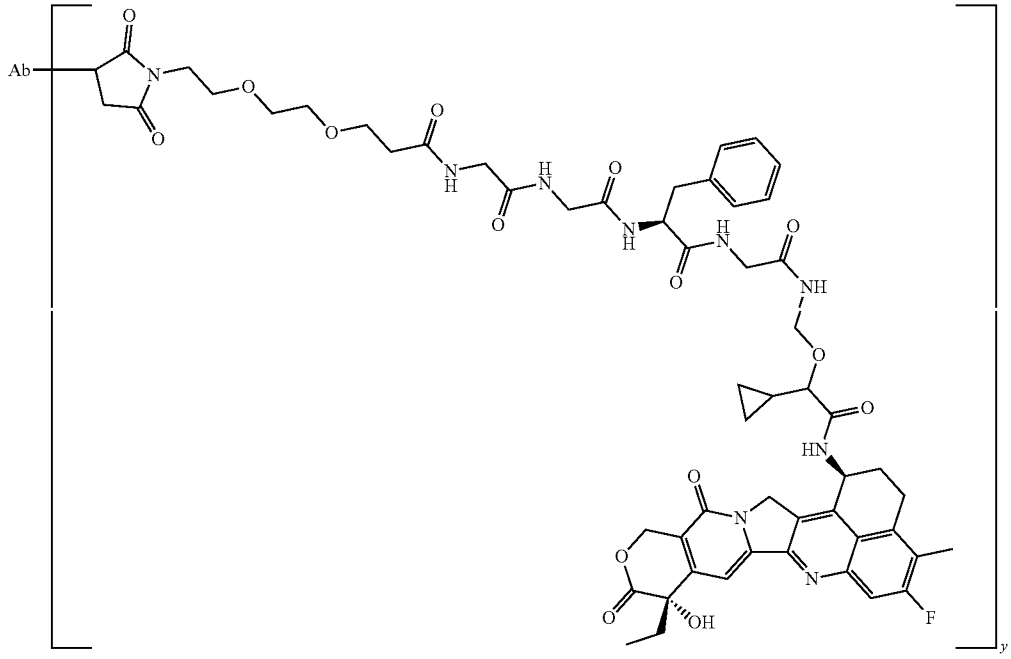

wherein Ab is the anti-BCMA antibody or the antigen-binding fragment as defined above, y is a number selected from 2 to 10, preferably a number selected from 4 to 10, more preferably, 4, 6, 8 or 10.

In a preferred embodiment of the present disclosure, the antibody drug conjugate or the pharmaceutically acceptable salt or solvate is as shown in general formula (III) or a pharmaceutically acceptable salt or solvate thereof;

(III)

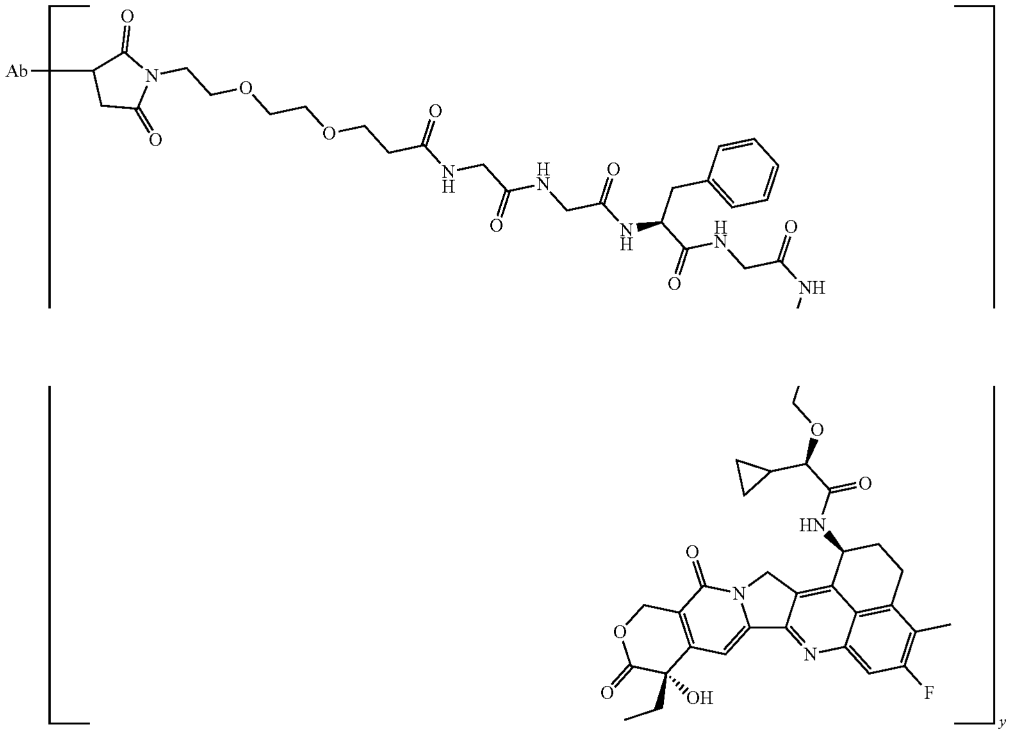

wherein Ab is the anti-BCMA antibody or the antigen-binding fragment as defined above, y is a number selected from 2 to 10, preferably a number selected from 4 to 10, more preferably, 4, 6, 8 or 10.

In a preferred embodiment of the present disclosure, the antibody drug conjugate or the pharmaceutically acceptable salt or solvate is selected from the group consisting of the following structures:

(ADC1)

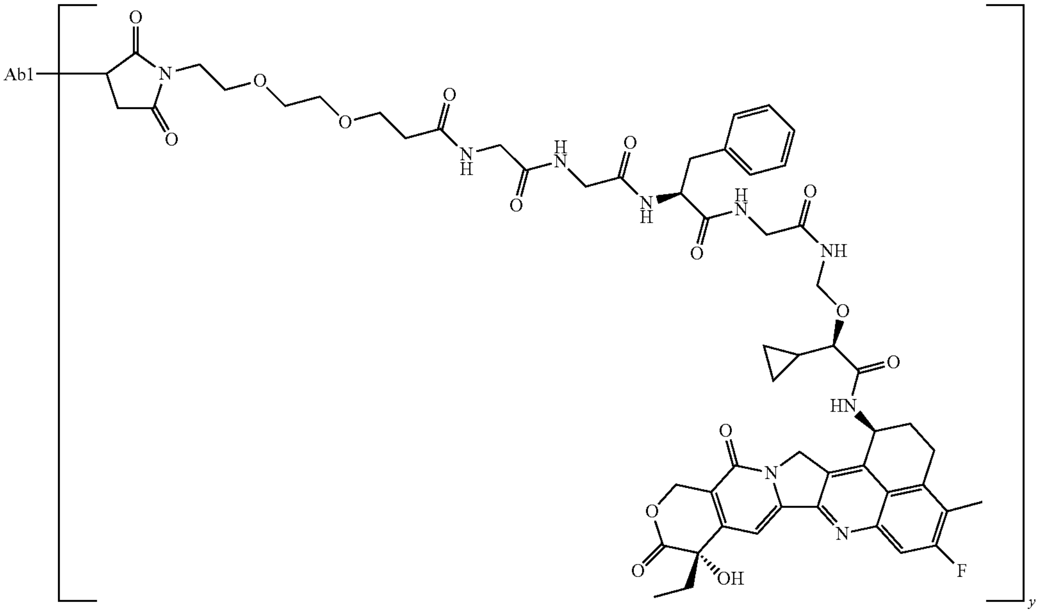

(ADC2)

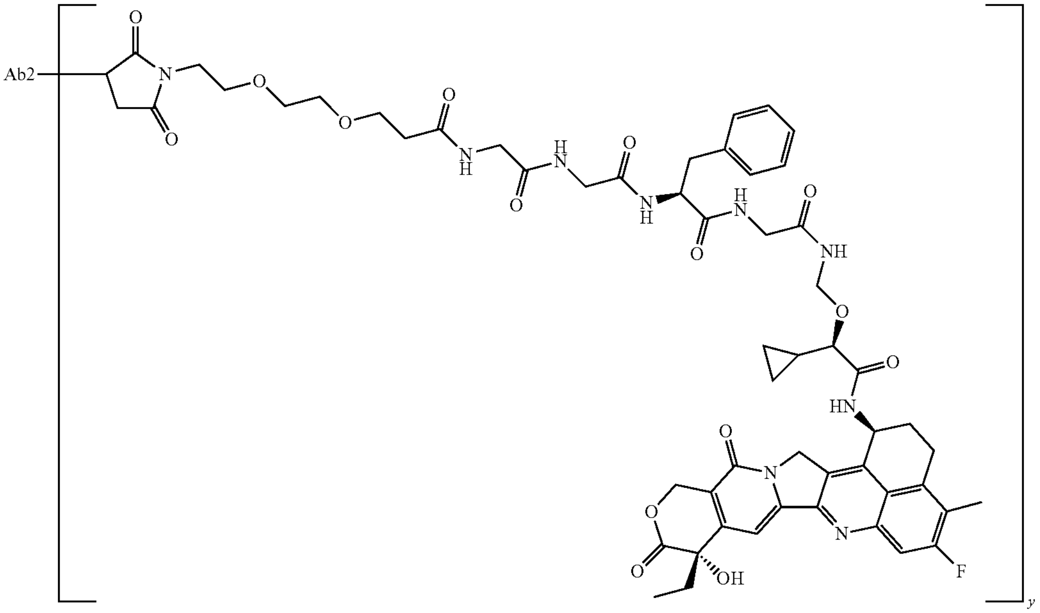

-continued
(ADC3)
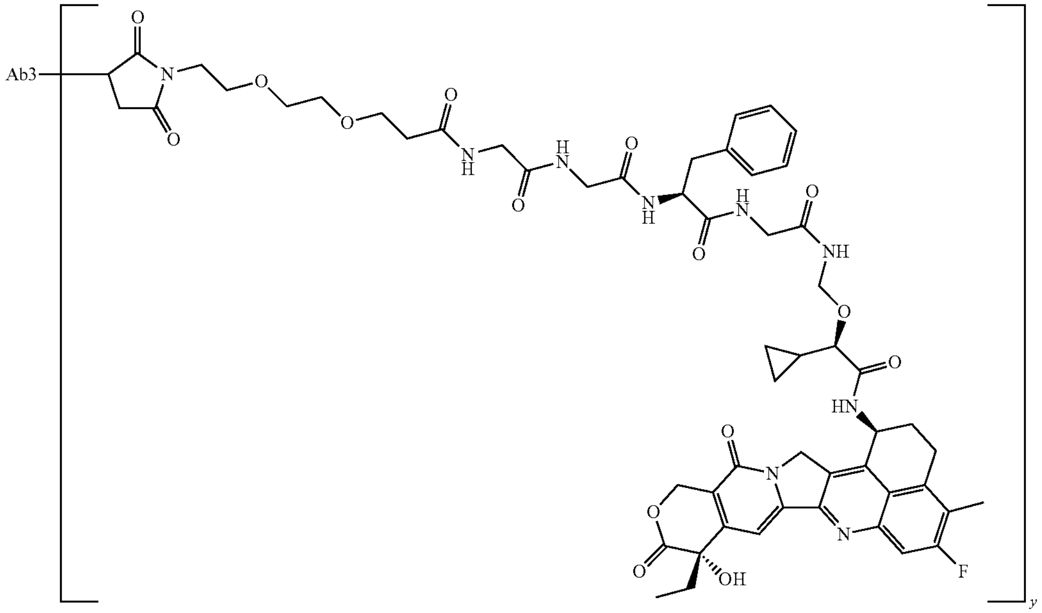
wherein, y is a number selected from 2 to 10, preferably a number selected from 4 to 10, more preferably, 4, 6, 8 or 10.
The present disclosure also provides a method for preparing the antibody drug conjugate of general formula (I) or the pharmaceutically acceptable salt or solvate thereof, which comprises the following steps:
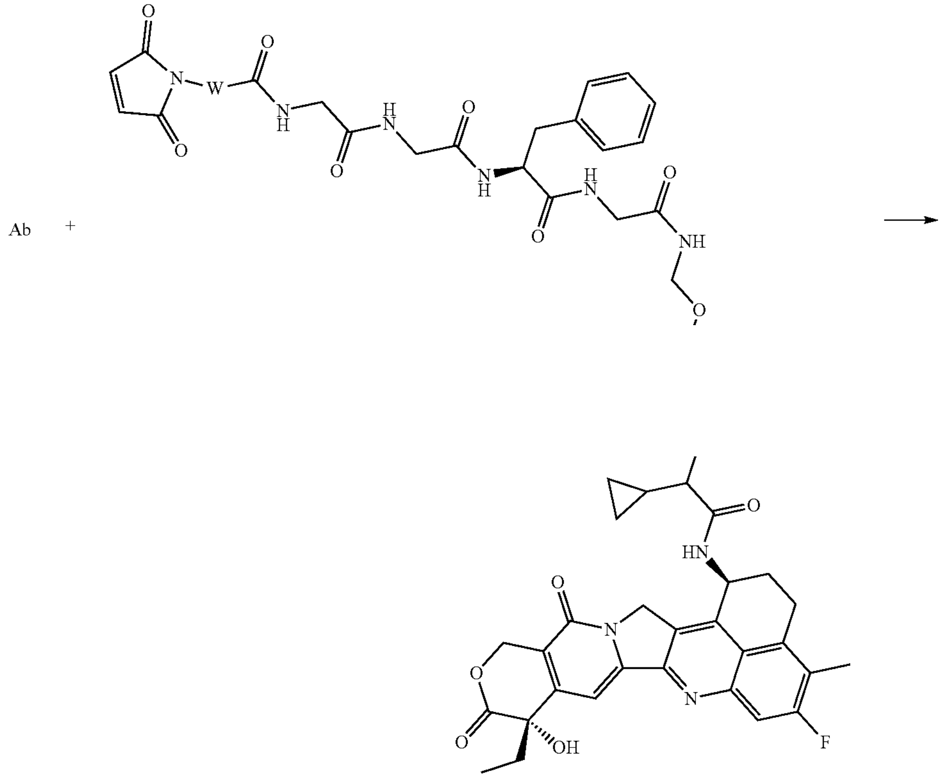
(F)

-continued

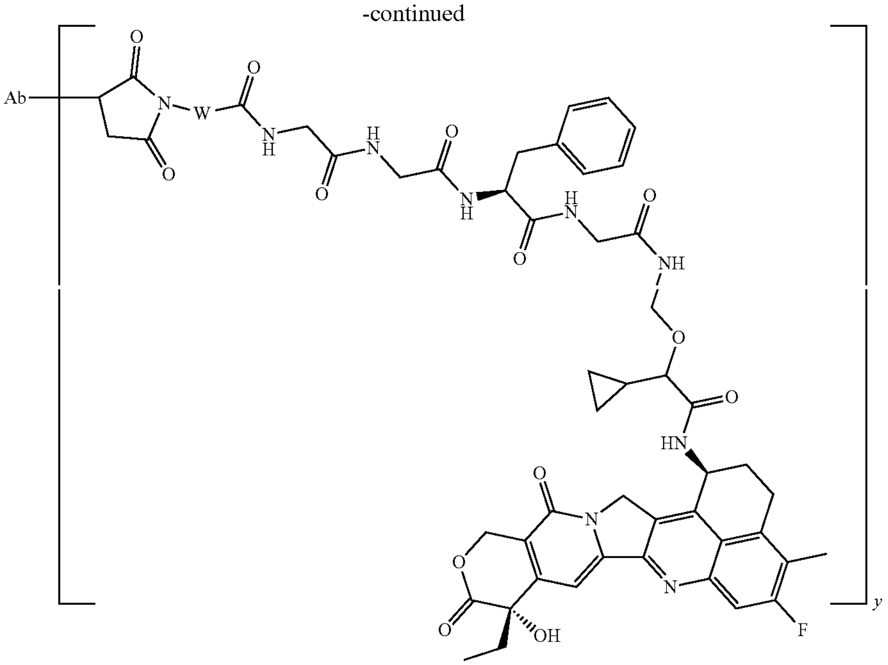

(I)

after Ab is reduced, it is subjected to coupling reaction with general formula (F) to obtain the compound of general formula (I);

wherein: W is as defined above.

Ab is the anti-BCMA antibody or the antigen-binding fragment as defined above, y is a number selected from 1 to 20, preferably a number selected from 4 to 10, more preferably, 4, 6, 8 or 10.

In another aspect, the present disclosure provides a pharmaceutical composition comprising the above mentioned antibody drug conjugate or the pharmaceutically acceptable salt or solvate thereof, and one or more pharmaceutically acceptable excipients, diluents or carriers.

In another aspect, the present disclosure relates to use of the above mentioned antibody drug conjugate or the pharmaceutically acceptable salt or solvate thereof, or the above mentioned pharmaceutical composition in the preparation of a medicament for treating or preventing a BCMA-mediated disease or condition.

In a preferred embodiment, the BCMA-mediated disease or condition is cancer or autoimmune disease; wherein the cancer is preferably a cancer expressing BCMA, more preferably lymphoma, leukemia or myeloma, and the autoimmune disease is preferably selected from the group consisting of lupus erythematosus, IgA nephropathy and rheumatic arthritis.

The antibody drug conjugate or pharmaceutically acceptable salt or solvate thereof of the present disclosure have significant anti-tumor effect and good safety, and have good metabolic activity in vivo, long drug duration in vivo, and broad prospects for clinical application.

DETAILED DESCRIPTION OF THE INVENTION

Terms

To make it easier to understand the present disclosure, certain technical and scientific terms are specifically defined below. Unless otherwise clearly defined elsewhere herein, all other technical and scientific terms used herein have the meanings commonly understood by those skilled in the art to which the present disclosure belongs.

The three-letter codes and one-letter codes of amino acids used in the present disclosure are as described in J. Biol. Chem, 243, p 3558 (1968).

The term "antibody" described in the present disclosure refers to an immunoglobulin, which is a tetrapeptide chain structure consisting of two identical heavy chains and two identical light chains linked by interchain disulfide bonds. The amino acid composition and order of arrangement of the immunoglobulin heavy chain constant regions are different, so their antigenicity is also different. According to this, immunoglobulins can be classified into five types, or known as isotypes of immunoglobulins, namely IgM, IgD, IgG, IgA and IgE, and their corresponding heavy chains are μ chain, δ chain, γ chain, α chain and ε chain, respectively. The same type of Ig can be classified into different subclasses according to the difference in the amino acid composition of the hinge region and the number and position of heavy chain disulfide bonds. For example, IgG can be classified into IgG1, IgG2, IgG3 and IgG4. The light chain is classified into κ chain or λ chain according to the difference in the constant region. Each of the five types of Ig can have κ chain or λ chain.

In the present disclosure, the antibody light chain according to the present disclosure can further comprise a light chain constant region, which comprises human or murine κ, λ chain or variant thereof.

In the present disclosure, the antibody heavy chain according to the present disclosure can further comprise heavy chain constant region, which comprises human or murine IgG1, IgG2, IgG3, IgG4 or variant thereof.

The sequence of about 110 amino acids near the N-terminus of the antibody heavy and light chains varies greatly and is the variable region (V region); the rest amino acid sequence near the C-terminus is relatively stable and is the constant region (C region). The variable region comprises 3 hypervariable regions (HVRs) and 4 framework regions (FRs) with relatively conservative sequences. The 3 hypervariable regions determine the specificity of the antibody, and they are also known as complementarity determining regions (CDRs). Each of the light chain variable region (VL) and heavy chain variable region (VH) consists of 3 CDR regions and 4 FR regions. The order of arrangement from the amino terminus to the carboxyl terminus is: FR1, CDR1, FR2, CDR2, FR3, CDR3, FR4. The 3 CDR regions of the light chain refer to LCDR1, LCDR2 and LCDR3; the 3 CDR regions of the heavy chain refer to HCDR1, HCDR2 and HCDR3. The number and position of the CDR amino acid residues in the VL region and VH region of the antibody or antigen-binding fragment according to the present disclosure comply with the known Kabat numbering criteria and Kabat, AbM or IMGT definition criteria (http://bioinf.org.uk/abs/).

The term "antigen presenting cell" or "APC" is a cell that presents foreign antigen complexed with MHC on its surface. T cells utilize T cell receptors (TCRs) to recognize such complexes. Examples of APCs include, but are not limited to, dendritic cells (DCs), peripheral blood mononuclear cells (PBMCs), monocytes, B lymphoblast and monocyte-derived dendritic cells.

The term "antigen presenting" refers to the process of capturing antigens by APCs and enabling them to be recognized by T cells, for example as a component of MHC-I/MHC-II conjugate.

The term "BCMA" includes any variant or isoform of BCMA that is naturally expressed by cells. The antibodies of the present disclosure can cross-react with BCMA derived from non human species. Alternatively, the antibodies can also be specific for human BCMA and may not show cross-reactivity with other species. BCMA or any variant or isoform thereof can be isolated from cells or tissues naturally expressing the same, or produced by recombinant techniques using techniques commonly used in the art and those described herein. Preferably, the anti-BCMA antibody targets human BCMA that has a normal glycosylation pattern.

The term "recombinant human antibody" includes human antibodies prepared, expressed, created or isolated by recombinant methods, and the techniques and methods involved are well known in the art, such as:

1. antibodies isolated from transgenic and trans-chromosomal animals (for example mice) with human immunoglobulin genes, or from hybridomas prepared therefrom;
2. antibodies isolated from host cells transformed to express the antibodies, such as transfectoma;
3. antibodies isolated from recombinant combinatorial human antibody libraries; and
4. antibodies prepared, expressed, created or isolated by methods such as splicing human immunoglobulin gene sequences with other DNA sequences.

Such recombinant human antibodies comprise variable region and constant region, which utilize specific human germline immunoglobulin sequences encoded by germline genes, but also comprise subsequent rearrangements and mutations such as those occur during antibody maturation.

The term "murine antibody" in the present disclosure is a monoclonal antibody against human BCMA prepared according to the knowledge and skills in the art. During preparation, the test subject is injected with BCMA antigen, and then hybridomas expressing antibody having the desired sequence or functional properties are isolated. In a preferred embodiment of the present disclosure, the murine BCMA antibody or the antigen-binding fragment thereof may further comprise the light chain constant region of murine κ, λ chain or variant thereof, or further comprise the heavy chain constant region of murine IgG1, IgG2, IgG3 or IgG4 or variant thereof.

The term "human antibody" includes antibodies having variable region and constant region of human germline immunoglobulin sequences. The human antibodies of the present disclosure may include ammo acid residues that are not encoded by human germline immunoglobulin sequences (such as mutations introduced by random or site-specific mutagenesis in vitro or by somatic mutations in vivo). However, the term "human antibody" does not include antibodies in which CDR sequences derived from the germline of another mammalian species (such as mice) have been grafted onto human framework sequences (namely "humanized antibodies").

The term "humanized antibody", also known as CDR-grafted antibody, refers to the antibody produced by grafting murine CDR sequences into the frameworks of human antibody variable region. Humanized antibody can overcome the shortcomings of strong immune responses induced by chimeric antibodies that carry a large amount of murine protein components. In order to avoid the decrease in activity caused by the decrease in immunogenicity, the human antibody variable regions can be subjected to minimal reverse mutation to maintain the activity.

The term "chimeric antibody" is an antibody formed by fusing the variable region of a murine antibody with the constant region of a human antibody, which can alleviate the immune response induced by murine antibody. Establishing a chimeric antibody requires first establishing a hybridoma that secretes murine specific monoclonal antibody, then cloning the variable region gene from the murine hybridoma cells, and then cloning the constant region gene of the human antibody as necessary, linking the murine variable region gene with the human constant region gene to form a chimeric gene, which is inserted into a human expression vector, and finally expressing the chimeric antibody molecule in a eukaryotic industrial system or a prokaryotic industrial system. The human antibody constant region can be selected from the heavy chain constant region of human IgG1, IgG2, IgG3 or IgG4 or variant thereof, preferably human IgG1, IgG2 or IgG4 heavy chain constant region, or IgG1 heavy chain constant region with enhanced ADCC (antibody-dependent cell-mediated cytotoxicity) after amino acid mutation.

The term "antigen-binding fragment" refers to antigen-binding fragment of an antibody and antibody analog, which usually comprises at least part of the antigen-binding region or variable region (for example one or more CDRs) of the parental antibody. The antibody fragment retains at least some of the binding specificity of the parental antibody. Generally, when the activity is represented on a mole basis, the antibody fragment retains at least 10% of the parental binding activity. Preferably, the antibody fragment retains at least 20%, 50%, 70%, 80%, 90%, 95% or 100% or more of the binding affinity of the parental antibody to the target. Examples of antigen-binding fragments include, but are not limited to: Fab, Fab', F(ab')2, Fv fragment, linear antibody, single-chain antibody, nanobody, domain antibody and multispecific antibody. Engineered antibody variants are reviewed in Holliger and Hudson, 2005, Nat. Biotechnol. 23: 1126-1136.

The "Fab fragment" consists of one light chain and the CH1 and variable regions of one heavy chain. The heavy chain of a Fab molecule cannot form disulfide bonds with another heavy chain molecule.

The "Fc" region comprises two antibody heavy chain fragments comprising the CH2 and CH3 domains. The two heavy chain fragments are held together by two or more disulfide bonds and through the hydrophobic interaction of the CH3 domain.

The "Fab' fragment" comprises a light chain and a part of a heavy chain comprising the VH domain, the CH1 domain and the region between the CH1 and CH2 domains, so that interchain disulfide bonds can be formed between the two heavy chains of two Fab' fragments, thereby forming a F(ab')2 molecule.

The "F(ab')2 fragment" comprises two light chains and two heavy chains comprising a part of the constant region between the CH1 and CH2 domains, thereby forming interchain disulfide bonds between the two heavy chains. Therefore, the F(ab')2 fragment consists of two Fab' fragments held together by disulfide bonds between the two heavy chains.

The "Fv region" comprises variable regions from both the heavy chain and the light chain, but lacks constant regions.

The term "multispecific antibody" is used in its broadest sense, encompassing antibodies with specificity for multiple epitopes. These multispecific antibodies include, but are not limited to: antibodies comprising heavy chain variable region VH and light chain variable region VL, wherein the VH-VL unit has specificity for multiple epitopes; antibodies with two or more VL and VH regions, each VH-VL unit binds to different targets or different epitopes of the same target; antibodies with two or more single variable regions, each single variable region binds to different targets or different epitopes of the same target; full-length antibodies, antibody fragments, diabodies, bispecific diabodies and triabodies, covalently or non-covalently linked antibody fragments, and the like.

The term "single-chain antibody" is a single-chain recombinant protein formed by linking the heavy chain variable region VH and light chain variable region VL of an antibody through a linker peptide. It is the minimum antibody fragment with complete antigen binding site.

The term "domain antibody fragment" is an immunoglobulin fragment having immunological functions, which comprises either the heavy chain variable region or the light chain variable region. In some cases, two or more VH regions are covalently linked by a peptide linker to form a bivalent domain antibody fragment. The two VH regions of the bivalent domain antibody fragment can target the same antigen or different antigens.

The term "binding to BCMA" in the present disclosure refers to being able to interact with human BCMA.

The term "antigen-binding site" in the present disclosure refers to a three-dimensional site recognized by the antibody or antigen-binding fragment of the present disclosure.

The term "epitope" refers to a site on an antigen that specifically binds to an immunoglobulin or antibody. Epitopes can be formed by adjacent amino acids or non-adjacent amino acids that are juxtaposed due to tertiary folding of the protein. Epitopes formed by adjacent amino acids are usually maintained after exposure to a denaturing solvent, while epitopes formed by tertiary folding are usually lost after treatment with a denaturing solvent. Epitopes usually comprise at least 3-15 amino acids in a unique spatial conformation. Methods for determining what epitope is bound to a given antibody are well known in the art, including immunoblotting, immunoprecipitation detection analysis and the like. Methods for determining the spatial conformation of an epitope include the techniques in the art and the techniques described herein, for example X-ray crystal analysis, two-dimensional nuclear magnetic resonance and the like.

The terms "specifically binds" and "selectively binds" used in the present disclosure refer to the binding of an antibody to an epitope on a predetermined antigen. Generally, when recombinant human BCMA is used as the analyte and an antibody is used as the ligand, when measured by surface plasmon resonance (SPR) technology in an instrument, the antibody binds to the predetermined antigen at an equilibrium dissociation constant ($K_D$) of about less than $10^{-7}$ M or even less, and its binding affinity to the predetermined antigen is at least twice as much as its binding affinity to non-specific antigens (such as BSA and the like) other than the predetermined antigen or closely related antigens. The term "antibody that recognizes antigen" can be used interchangeably with the term "antibody that specifically binds to" herein.

The term "cross-reaction" refers to the ability of the antibodies of the present disclosure binding to BCMA derived from different species. For example, an antibody of the present disclosure that binds to human BCMA can also bind to BCMA of another species. Cross-reactivity is measured in binding assays (for example SPR and ELISA) by detecting specific reactivity with purified antigen, or the binding or functional interaction with cells that physiologically express BCMA. Methods for determining cross-reactivity include standard binding assays as described herein, for example surface plasmon resonance (SPR) analysis or flow cytometry.

The terms "inhibition" or "blocking" can be used interchangeably and encompass both partial and complete inhibition/blocking. The inhibition/blocking of a ligand preferably reduces or alters the normal level or type of activity that occurs when ligand binding occurs without inhibition or blocking. Inhibition and blocking are also intended to include any measurable reduction in binding affinity of the ligand when contacting with anti-BCMA antibody, compared to the ligand not contacting with anti-BCMA antibody.

The term "inhibition of growth" (for example, of cells) is intended to include any measurable reduction in cell growth.

The terms "induced immune response" and "enhanced immune response" can be used interchangeably and refer to the immune response stimulated (i.e. passive or adaptive) by a specific antigen. The term "induce" for inducing CDC or ADCC refers to stimulating a specific direct cell killing mechanism.

The "ADCC" in the present disclosure, i.e. antibody-dependent cell-mediated cytotoxicity, means that cells expressing Fc receptors directly kill the target cells coated with antibodies by recognizing the Fc segment of the antibodies. The ADCC function of antibodies can be enhanced, reduced or eliminated by modifying the Fc segment of IgG. The modification refers to mutation in the heavy chain constant region of an antibody.

The methods for producing and purifying antibodies and antigen-binding fragments are well-known and can be found in the prior art, such as Antibodies: A Laboratory Manual, Cold Spring Harbor, chapters 5-8 and 15. For example, mice can be immunized with human BCMA or fragment thereof, and the obtained antibodies can be renatured and purified, and subjected to amino acid sequencing by using conventional methods. Antigen-binding fragments can also be prepared by using conventional methods. The antibody or antigen-binding fragment of the present invention is genetically engineered to add one or more human FR region(s) to the non-human CDR regions. The human FR germline sequences can be obtained from the ImmunoGeneTics (IMGT) website http://imgt.cines.fr, or from The Immunoglobulin FactsBook, 2001ISBN012441351.

The engineered antibodies or antigen-binding fragments of the present disclosure can be prepared and purified by conventional methods. The cDNA sequences of the corresponding antibodies can be cloned and recombined into GS expression vectors. The recombinant immunoglobulin expression vectors can stably transfect CHO cells. As a more recommended prior art, mammalian expression systems can lead to glycosylation of antibodies, especially at the highly conserved N-terminus of the Fc region. Stable clones are obtained by expressing antibodies that specifically bind to human antigens. Positive clones are expanded in serum-free medium of bioreactors to produce the antibodies. The culture fluid into which the antibodies are secreted can be purified and collected by conventional techniques. The antibodies can be filtered and concentrated by conventional methods. Soluble mixtures and multimers can also be removed by conventional methods, for example molecular sieves and ion exchange. The resulting product needs to be frozen immediately, for example at −70 °C, or lyophilized.

The antibody of the present disclosure refers to monoclonal antibody. The monoclonal antibody (mAb) in the present disclosure refers to an antibody obtained from a single cloned cell strain, which is not limited to a eukaryotic, prokaryotic or phage cloned cell strain. Monoclonal antibodies or antigen-binding fragments can be obtained by recombination using, for example, hybridoma technology, recombination technology, phage display technology, synthetic technology (such as CDR-grafting) or other existing technologies.

"Administering", "giving," and "treating", when applied to animals, humans, experimental subjects, cells, tissues, organs or biological fluids, refer to contacting the exogenous medicament, therapeutic agent, diagnostic agent or composition with the animals, humans, subjects, cells, tissues, organs or biological fluids. "Administering", "giving" and "treating" can refer to for example treatment, pharmacokinetics, diagnostic, research and experimental methods. Treating cells includes contacting reagents with the cells, and contacting reagents with fluids, wherein the fluids are in contact with the cells. "Administering", "giving" and "treating" also refer to treating for example cells with reagents, diagnostic agents, binding compositions or with another cell in vitro and ex vivo. "Treating", when applied to human, veterinary or research subjects, refers to therapeutic, preventive or prophylactic measures, research and diagnostic applications.

"Treatment" refers to giving an internal or external therapeutic agent, for example comprising any one of the antibodies of the present disclosure, to a patient having one or more disease symptom(s) on which the therapeutic agent is known to have therapeutic effect. Generally, the therapeutic agent is given in an amount effective to alleviate one or more disease symptom(s) in the treated subject or population, either to induce the regression of such symptoms or to inhibit the development of such symptoms to any clinically measurable extent. The amount of therapeutic agent that is effective to alleviate any specific disease symptom (also referred to as a "therapeutically effective amount") can vary according to a variety of factors, for example the disease state, age and body weight of the patient, and the ability of the drug to produce the desired therapeutic effect in the patient. Whether the disease symptoms have been alleviated can be evaluated by any clinical testing methods commonly used by doctors or other health care professionals for evaluating the severity or progression of the symptoms. Although the embodiments of the present disclosure (for example treatment methods or products) may be ineffective in alleviating each disease symptom of interest, but they should reduce the disease symptom of interest in a statistically significant number of patients, as determined by any statistical testing methods known in the art, such as Student t-test, chi-square test, Mann and Whitney's U test, Kruskal-Wallis test (H test), Jonckheere-Terpstra test and Wilcoxon test.

The term "essentially consisting of . . . " or variant thereof used throughout the specification and claims means to comprise all the elements or element groups described, and optionally comprise other elements similar or different in nature to the elements described, which does not significantly change the basic or new properties of the given closing regimen, method or composition.

The term "naturally occurring" applied to a certain object in the present disclosure refers to the fact that the object can be found in nature. For example, a polypeptide sequence or polynucleotide sequence that exists in organisms (including viruses) that can be isolated from natural sources and has not been intentionally modified artificially in the laboratory is naturally occurring.

The "effective amount" includes an amount sufficient to ameliorate or prevent a symptom or condition of a medical condition. The effective amount also refers to an amount sufficient to allow or facilitate diagnosis. The effective amount for a particular patient or veterinary subject can vary depending on the following factors: such as the condition to be treated, the general health condition of the patient, the method, route and dose of drug administration, and the severity of side effects. The effective amount can be the maximum dose or dosing regimen that avoids significant side effects or toxic effects.

"Exogenous" refers to substances produced outside organisms, cells or human bodies depending on backgrounds.

"Endogenous" refers to substances produced inside cells, organisms or human bodies depending on backgrounds.

"Identity" refers to the sequence similarity between two polynucleotide sequences or between two polypeptides. When the positions in the two sequences aligned are occupied by the same base or amino acid monomer subunit, for example if each position of two DNA molecules is occupied by adenine, then the molecules are homologous at that position. The identity percentage between two sequences is a function of the number of matching or homologous positions shared by the two sequences divided by the number of positions to be compared×100%. For example, in the optimal sequence alignment, if 6 out of 10 positions in the two sequences are matched or homologous, then the two sequences are 60% homologous. Generally, the alignment is made when two sequences are aligned to obtain the maximum identity percentage.

The expressions "cell", "cell line" and "cell culture" used herein can be used interchangeably, and all such names include progeny thereof. Therefore, the words "transformant" and "transformed cell" include primary test cells and cultures derived therefrom, regardless of the number of passages. It should also be understood that due to intentional or unintentional mutations, all offspring cannot be exactly the same in terms of DNA content. Mutant progeny with the same function or biological activity as screened in the original transformed cells is included. It can be clearly seen from the context when different names are referred to.

"Optional" or "optionally" means that the event or circumstance described subsequently can but not necessarily occur, and the description includes the cases where the event or circumstance does or does not occur. For example, "optionally comprising 1 to 3 antibody heavy chain variable regions" means that the antibody heavy chain variable regions of particular sequences can but need not be present.

The "pharmaceutical composition" means comprising one or more of the antibody (antibodies) or antigen-binding fragment(s) described herein as well as other components such as physiological/pharmaceutically acceptable carriers and excipients. The objective of the pharmaceutical composition is to facilitate administration of a compound to an organism, which is conducive to the absorption of the active ingredient so as to show the biological activity.

The term "pharmaceutical salt" refers to a salt of the antibody drug conjugates of the present disclosure. Such salts are safe and effective when used in mammalians and possess the required biological activity. The ligand drug conjugate of the present disclosure at least comprises one amino group and thus may form a salt with an acid. Non-limiting examples of pharmaceutically acceptable salts include: hydrochloride, hydrobromide, hydriodate, sulphate, bisulfate, citrate, acetate, succinate, ascorbate, oxalate, nitrate, sorbate, hydrophosphate, dihydrophosphate, salicylate, hydrocitrate, tartrate, maleate, fumarate, formate, benzoate, mesylate, ethanesulfonate, benzenesulphonate and p-toluenesulfonate.

The term "solvate" refers to a pharmaceutically acceptable solvate formed by the antibody-drug conjugate compound of the present disclosure and one or more solvent molecule(s). Non-limiting examples of solvent molecules include water, ethanol, acetonitrile, isopropanol, ethyl acetate.

The term "cytotoxic drug", when used in the present disclosure, refers to a substance that inhibits the function of cells and/or causes cell death or destruction.

The "tubulin inhibitor" refers to a class of compounds that interfere with the process of cell mitosis by inhibiting the polymerization of tubulin or promoting the aggregation of tubulin, thereby exerting an anti-tumor effect. Non-limiting examples thereof include: maytansinoids, calicheamicin, taxanes, vincristine, colchicine, dolastatin/auristatin/monomethyl auristatin E (MMAE)/monomethyl auristatin F (MMAF).

"Linker" refers to a chemical moiety by which an antibody is covalently attached to a covalent bond or atomic chain of a drug. Non-limiting examples of linkers include: arylene, heteroarylene, PEG, polymethyleneoxy, succinate, succinamide, diglycolate, malonate and caproamide.

"Drug load" (DAR) is represented by y, which is the average number of cytotoxic drugs per antibody in formula (A). The range of drug load in the present invention can be 1-20 cytotoxic drugs (D) per antibody. The antibody-drug conjugate of general formula (A) is a collection of antibodies conjugated to a certain range (1-20) of cytotoxic drugs. The drug load (DAR) in an antibody-drug conjugate from coupling reaction can be characterized by conventional means, for example mass spectrometry, HPLC and ELISA. By these means, the quantitative distribution of the antibody-drug conjugate on the y value can be determined.

The present disclosure also comprises the compounds of formula (I) in various deuterated forms. Each of the available hydrogen atoms attached to the carbon atom can be independently replaced by a deuterium atom. Those skilled in the art can synthesize a compound of formula (I) in a deuterated form with reference to the relevant literatures. The compound of formula (I) in deuterated form can be prepared by employing commercially available deuterated raw materials, or they can be synthesized by conventional techniques with deuterated reagents including, but not limited to, deuterated borane, trideuterated borane in tetrahydrofuran, deuterated lithium aluminum hydride, deuterated iodoethane, deuterated iodomethane and the like.

The term "pharmaceutical composition" refers to a mixture of one or more of the compounds described herein or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity. The preparation of conventional pharmaceutical compositions can be found in the Chinese Pharmacopoeia.

The term "pharmaceutically acceptable salt" or "pharmaceutical salt" refers to a salt of the ligand-drug conjugate of the present disclosure or a salt of the compound of the present disclosure, which is safe and effective in mammals and has the desired biological activity. The ligand-drug conjugate of the present disclosure contains at least one amino, so it can form a salt with an acid. Non-limiting examples of pharmaceutically acceptable salts include hydrochloride, hydrobromide, hydroiodide, sulfate, bisulfate, citrate, acetate, succinate, ascorbate, oxalate, nitrate, sorbate, hydrogen phosphate, dihydrogen phosphate, salicylate, hydrogen citrate, tartrate, maleate, fumarate, formate, benzoate, methanesulfonate, ethanesulfonate, benzenesulfonate, p-toluenesulfonate.

The term "drug loading" refers to the average number of cytotoxic drugs loaded on each antibody or antigen-binding fragment thereof in the compound of formula (V), and can also be expressed as the ratio of the number of drug to the number of antibody. The drug loading can range from 0 to 12, preferably from 1 to 10 cytotoxic drugs (D) per ligand. In an embodiment of the present invention, the drug loading is expressed as y, also known as DAR value, and exemplary values can be an average of 1, 2, 3, 4, 5, 6, 7, 8, 9, 10. The average number of drugs per ADC molecule after coupling reaction can be determined by conventional identification methods such as UV/visible spectroscopy, mass spectrometry, ELISA test and HPLC.

In an embodiment of the present invention, the cytotoxic drug is conjugated to the N-terminal amino and/or the ε-amino of lysine residues of the ligand via a linking unit. In an embodiment of the present invention, the cytotoxic drug is conjugated to the sulfhydryl group of the ligand via a linking unit. Typically, the number of drug molecules conjugated to the antibody in a coupling reaction will be less than the theoretical maximum.

The following non-limiting methods can be used to control the loading of the ligand-cytotoxic drug conjugates:

(1) controlling the molar ratio of the linking reagent to the monoclonal antibody, (2) controlling the reaction time and temperature, (3) selecting different reaction reagents.

The antibody drug conjugate or pharmaceutical salt or solvent thereof in the present disclosure has significant anti-tumor effects and good safety.

EXAMPLES

The examples are incorporated below for further description of the present invention, but these examples do not limit the scope of the present invention. The experimental methods with unspecified conditions in the examples of the present invention generally follow conventional conditions, such as those in Antibodies: A Laboratory Manual and Molecular Cloning: A Laboratory Manual, Cold Spring Harbor; or according to the conditions recommended by the raw material or product manufacturer.

The experimental methods in the examples of the present disclosure for which the specific conditions are not indicated were carried out according to conventional conditions or the conditions recommended by the material or product manufacturers. The reagents for which the specific sources are not indicated are conventional reagents purchased from market.

The known raw materials of the present disclosure can be synthesized by or in accordance with the methods known in the art, or can be purchased from Jiangsu Aikon etc. As shown in the following table:

| Product name | Company | Item No: |
|---|---|---|
| DBU | Energy chemical | HA090231 |
| DCM | Lian Yu | 2020092301 |
| Compound d | Jiangsu Aikon | AK20-58300 |
| HATU | Bide | ARC064 |

Example 1-1: The Synthesis of Compound a a

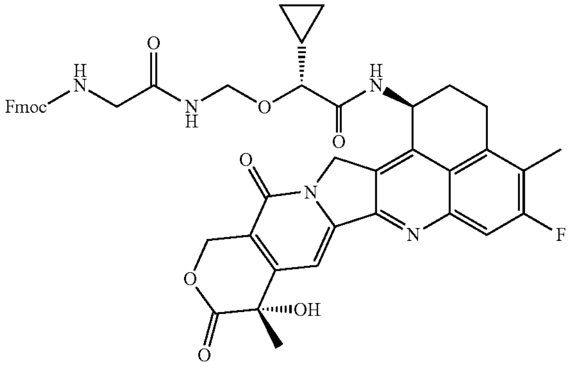

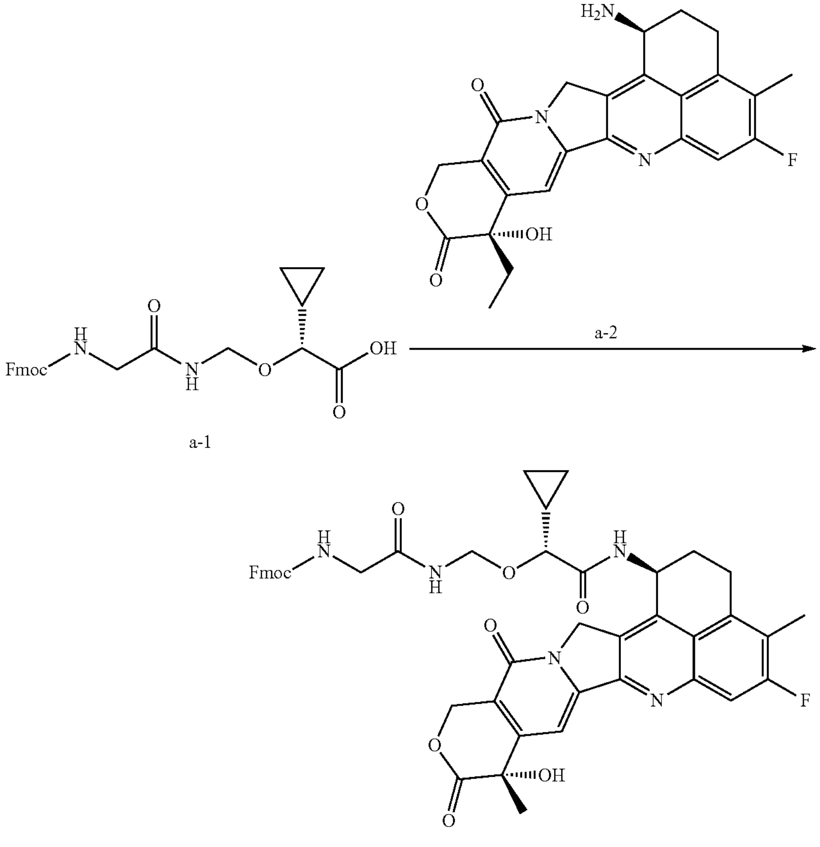

a-2 a-1 a

Raw material a-1 (4.1 g, 9.71 mmol) and raw material a-2 (4.3 g, 8.09 mmol, containing 4% amino isomer impurity) were placed in a 250 mL reaction bottle. DCM (54 mL) and MeOH (18 mL) were added under nitrogen protection, stirred and cooled to 0 °C. DMTMM (3.6 g, 12.1 mmol) and triethylamine (2.5 g, 24.2 mmol) were added, and stirring reaction was maintained at 0 °C for 1 h. HPLC central control showed that the material a-2 was completely reacted, and the reaction liquid was dried by reducing pressure (<25 °C). MTBE (120 mL) was added to stir beating (sludge). The solution was poured out and filtered, 120 mL MTBE was added to the sludge again for beating (solid), filtered, washed the filter cake with water (60 mL×2), and dried to obtain the coarse product, and the coarse product was dissolved in dichloromethane and methanol. Compound a (6.2 g, 7.37 mmol) was isolated by running two rounds of wet column chromatography (eluent DCM:MeOH=40:1-20:1) with purity of 99.3% and yield of 91%.

Example 1-2: The Synthesis of Compound b b

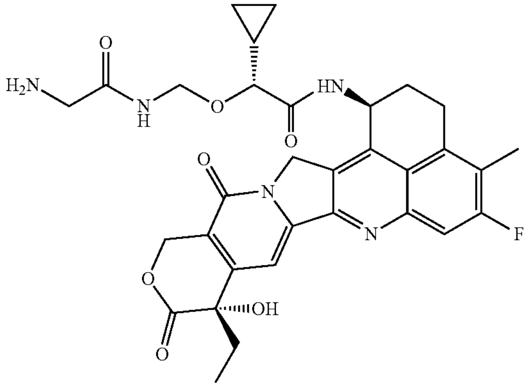

-continued

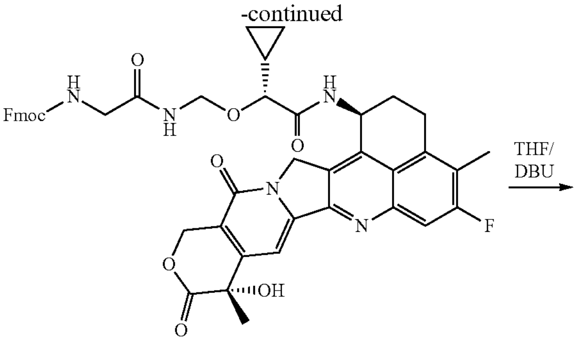

a

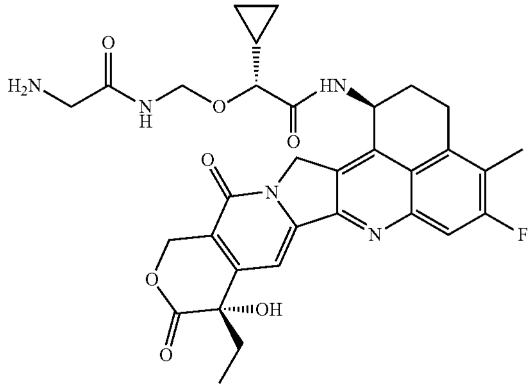

b

Compound a (5.7 g, 6.77 mmol) was placed into a 500 ml three necked bottle, dry THF (114 ml) was introduced under the protection of nitrogen, stirred to dissolve and cooled the internal temperature to about −10 °C. DBU (3.09 g, 20.31 mmol) was added by dripping for 5 min, the internal temperature was maintained at −10 to −5 °C during dripping. After dripping, the internal temperature was maintained at −10 to −5 °C, the reaction lasted for 2.5 h, and the solid precipitated.

The internal temperature was cooled to −20 °C, MTBE (114 mL) was added, and the internal temperature was maintained at −20 to −10 °C during the period. The product was completely precipitated and filtered, and the filter cake was washed with MTBE (57 mL×2). After being drained, 6 g crude compound b was obtained and stored at −78 °C for later use.

Example 1-3: The Synthesis of Compound e e

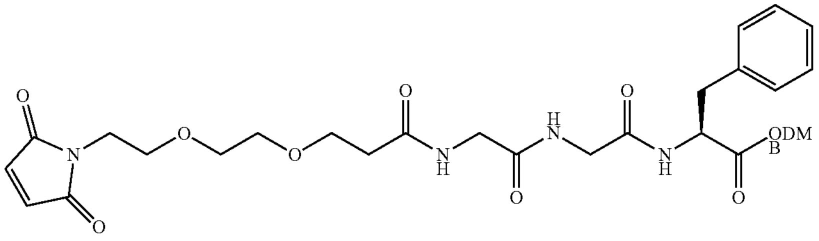

-continued

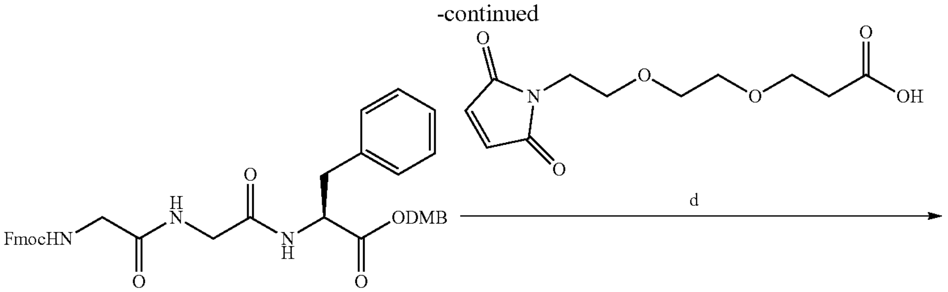

c e

Compound e (651 mg, 1 mmol) was dissolved in 10 mL DCM, stirring was started in the ice bath, and DBU (456 mg, 3 mmol) was added by dripping. The reaction was completed after one hour in the ice bath, and the compounds d (257 mg, 1 mmol) and HATU (420 mg, 1.1 mmol) were added sequentially. Stirring was performed in ice bath for 30 minutes, LCMS showed that the reaction was complete. The reaction solution was concentrated at 25 °C, and the residue was purified by column machine (ACN in $H_2O$, 50% of the product) to obtain compound e, reddish brown solid, 130 mg, with a yield of 19%.

MS: 691.3 [M+23].

Example 1-4: The Synthesis of Compound f f

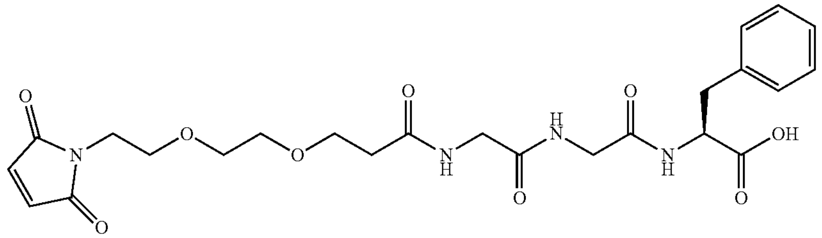

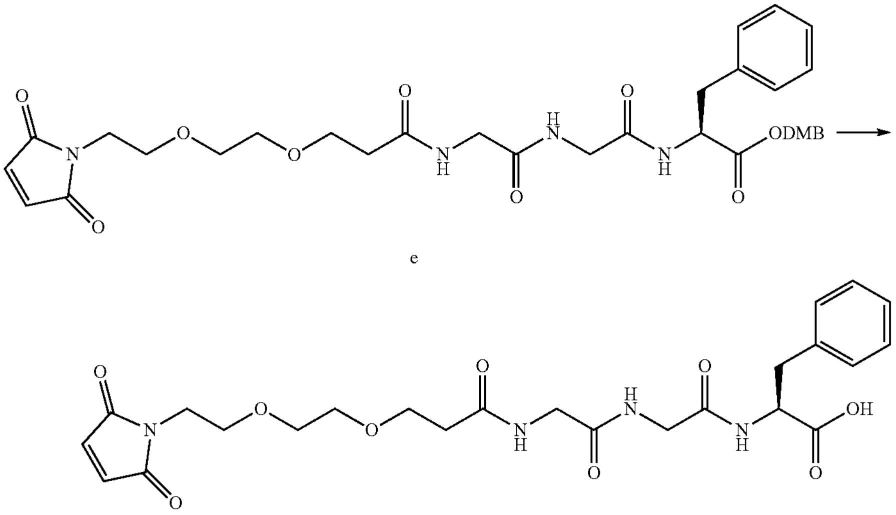

e f

Compound e (130 mg, 0.19 mmol) was dissolved in DCM, anisole (62 mg, 0.57 mmol) and dichloroacetic acid (245 mg, 1.9 mmol) were added, and the reaction was stirred at room temperature overnight for 16 hours. Sampling, LC-MS central control showed that raw materials were completely consumed, and the reaction was stopped. The reaction solution was concentrated at 25 °C, and the residue was purified by the column machine of reverse phase column (ACN/$H_2O$, 30% of the product) to obtain compound f, pink solid, 53 mg, with a yield of 54%.

MS: 519.2 [M+1].

Example 1-5: The Synthesis of Compound d

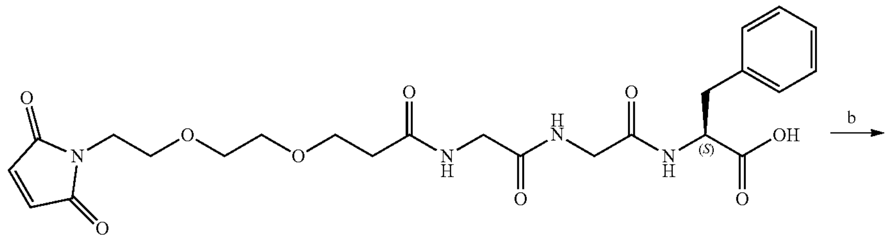

f

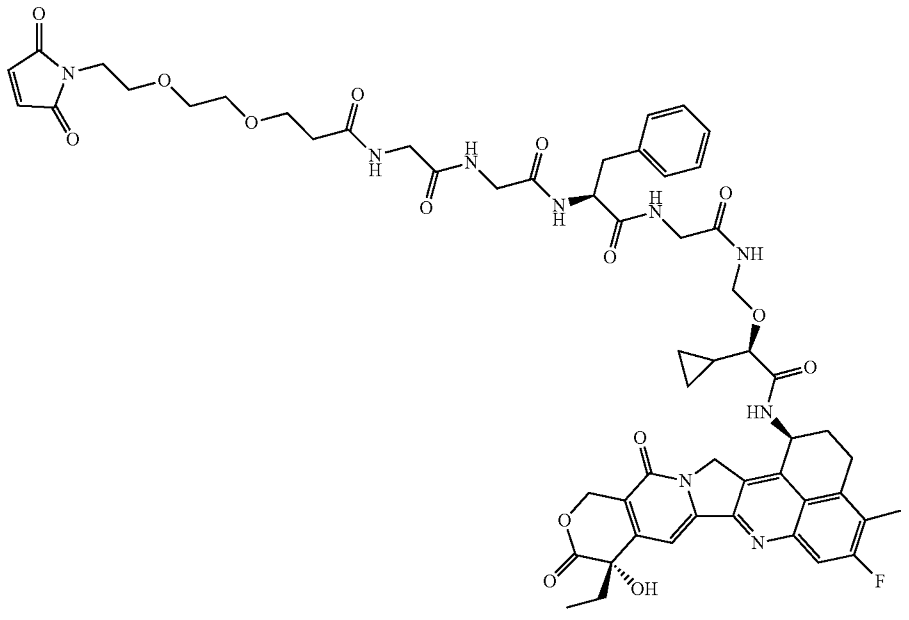

D

Compound f (23 mg, 0.044 mmol) and compound b (27 mg, 0.044 mmol) were dissolved in DCM (3 mL) and MeOH (1 mL) and cooled to −30 °C under nitrogen protection. DMTMM (20 mg, (0.067 mmol) was added, and the reaction was performed at a controlled temperature of −20 °C to −10 °C for 1 hour. Sampling, LC-MS central control showed that the raw material was completely consumed. The temperature was maintained at −10 °C, 10 mL water was added to quench the reaction, 30 mL DCM was added for separation by stratification. The aqueous phase was extracted with DCM/MeOH=10/1 (50 mL). The organic phase was pooled, dried with anhydrous sodium sulfate and concentrated under reduced pressure at 25 °C. The residue was purified (ACN/$H_2O$/0.05% FA) to obtain compound d, 5.8 mg white solid with yield of 12% and purity of 98.87% by HPLC.

MS: 1120.3 [M+1].

Example 2: Preparation of Antigens

The protein encoding the His-tagged extracellular domain of human BCMA (BCMA-His) was synthesized by Sino-Biologics (Cat No.: 10620-H08H).

Sequence of BCMA-His:

```
                                      SEQ ID NO: 21
MLQMAGQCSQNEYFDSLLHACIPCQLRCSSNTPPLTCQRYCNASVTNSV

KGTNAHHHHHHHHHHH.
```

Example 3: Obtaining Murine Hybridomas and Antibody Sequences

A total of 5 Balb/c and 5 A/J female 10-week-old mice were immunized with the human antigen BCMA-His. Sigma Complete Freund's Adjuvant (CFA) and Sigma Incomplete Freund's Adjuvant (IFA) were used. The immunogen and the immune adjuvant were thoroughly mixed at a ratio of 1:1 and emulsified to make a stable "water-in-oil" liquid. The injection dose was 25 μg/200 μL/mouse.

TABLE 1

| Immunization scheme | |
|---|---|
| Day 01 | First immunization, complete Freund's adjuvant |
| Day 21 | Second immunization, incomplete Freund's adjuvant |
| Day 35 | Third immunization, incomplete Freund's adjuvant |
| Day 42 | Blood sampling and serum titer test (blood after 3 immunizations) |
| Day 49 | Fourth immunization, incomplete Freund's adjuvant |
| Day 56 | Blood sampling and serum titer test (blood after 4 immunizations) |

The serum titer and the ability to bind to cell surface antigens of the serum of immunized mice were evaluated by using indirect ELISA method according to Example 3. The start of cell fusion was determined according to the detection results of titer (greater than 100,000 times of dilution). The immunized mice with high serum titer, affinity and FACS binding were selected for one final immunization and then sacrificed. The spleen cells were fused to SP2/0 myeloma cells and plated to obtain hybridomas. The hybridomas of interest were screened by indirect ELISA and established as monoclonal cell strains by limiting dilution method. The resulting antibody-positive strains were further screened by indirect ELISA so as to select the hybridomas that bind to the recombinant protein. Hybridoma cells at logarithmic growth phase were collected. RNA was extracted with Trizol (Invitrogen, 15596-018) and subjected to reverse transcription (PrimeScript™ Reverse Transcriptase, Takara #2680A). The cDNA obtained by reverse transcription was amplified by PCR using a mouse Ig-primer set (Novagen, TB326 Rev.B 0503). Finally, the sequence of murine antibody M1 was obtained.

The heavy chain and light chain variable region sequences of murine monoclonal antibody M1 are as follows:

```
M1 HCVR
                                      SEQ ID NO: 1
QVQLQQSGAELVRPGASVKLSCKALGYSFSDYEMHWVRQTPVHGLEWIG

GIHPGSGGSAYNQKFKGKATLTVDKSSSTAYMELSSLTSEDSAVYYCTR

LDYGYSWAWFPYWGQGTLVTVSA

M1 LCVR
                                      SEQ ID NO: 2
EILLTQSPAIIVTSPGEKVTITCSASSSVIYMNWYQQKPGSSPKIWIYG

ISNLASGVPARFSGSGSGTSFSFTINSMEAEDVATYYCQQRSSYPLTFG

AGTKLELK
```

TABLE 2

The CDR sequences of the heavy chain and light chain variable regions of murine monoclonal antibody M1 (according to Kabat numbering system)

| Name | Sequence | NO. |
|---|---|---|
| HCDR1 | DYEMH | SEQ ID NO: 3 |
| HCDR2 | GIHPGSGGSAYNQKFKG | SEQ ID NO: 4 |
| HCDR3 | LDYGYSWAWFPY | SEQ ID NO: 5 |
| LCDR1 | SASSSVIYMN | SEQ ID NO: 6 |
| LCDR2 | GISNLAS | SEQ ID NO: 7 |
| LCDR3 | QQRSSYPLT | SEQ ID NO: 8 |

Examples 4: Detection Method for In Vitro Binding Activity of Antibodies (1) In Vitro Indirect ELISA Binding Assay:

BCMA His protein (Sino Biological Inc., cat #10620-H08H) was diluted with pH 7.4 PBS to a concentration of 1 μg/ml, added to a 96-well high-affinity ELISA plate at 100 μl/well and incubated in a refrigerator at 4 °C overnight (16-20 hours). After washing the plate 4 times with PBST (pH 7.4 PBS containing 0.05% Tween-20), 3% bovine serum albumin (BSA) blocking solution diluted with PBST was added at 150 μl/well and incubated at room temperature for 1 hour for blocking. After completion of the blocking, the blocking solution was discarded, and the plate was washed 4 times with PBST buffer.

The antibody to be tested was 10-fold gradient diluted with PBST containing 3% BSA with the initial concentration of 1 μM to obtain 10 dilutions which were added to the microtiter plate at 100 μl/well and incubated at room temperature for 1 hour. After completion of the incubation, the plate was washed 4 times with PBST. HRP-labeled goat-anti-human secondary antibody (Abcam, Cat #ab97225) diluted with PBST containing 3% BSA was added at 100 μl/well and incubated at room temperature for 1 hour. The plate was washed 4 times with PBST, and then TMB chromogenic substrate (Cell Signaling Technology, cat #7004S) was added at 100 μl/well and incubated at room temperature in the dark for 1 minute. The stop solution (Cell Signaling Technology, cat #7002S) was added at 100 μl/well to terminate the reaction. The absorbance value at 450 nm was read with a microplate reader (BioTek, model Synergy H1). The data were analyzed. The results were analyzed by plotting the concentration-signal curve, as shown in the following table:

TABLE 3

| Affinity of murine antibodies to human BCMA antigen ($EC_{50}$ value) | |
|---|---|
| Murine antibody | $EC_{50}$ (nM) of the binding to human BCMA His antigen |
| M1 | 0.53 |

(2) In Vitro Cell Binding Assay:

The cultured cells with high BCMA expression (HEK-293T cells overexpressing BCMA; tumor cells expressing BCMA, NCI-H929) were collected. The cell density was adjusted and the cells were plated on a 96-well U-bottomed plate at $1\times10^5$ to $2\times10^5$ cells per well. The plate was centrifuged at 1200 g for 5 min and the supernatant was removed. 100 μl of gradient diluted antibody solution or mouse immunized serum was added and incubated at 4 °C for 60 min. The plate was centrifuged at 1200 g for 5 min and the supernatant was removed. The cells were washed twice with PBS. A fluorescently labeled secondary antibody (PE-GAH or PE-GAM) was added at 100 μl per well and incubated at 4 °C for 60 min. The plate was centrifuged at 1200 g for 5 min and the supernatant was removed. The cells were washed twice with PBS and then re-suspended in PBS. The signal was detected by using a flow cytometer, and a concentration curve was plotted for result analysis.

TABLE 4

| Affinity of murine antibodies to cells expressing BCMA ($EC_{50}$ value) | | |
|---|---|---|
| Murine antibody | $EC_{50}$ (nM) of the binding to HEK-293T/BCMA cells | $EC_{50}$ (nM) of the binding to NCI-H929 cells |
| M1 | 115.3 | 128.2 |

Example 5: Humanization Experiment of Murine Antibodies

Humanization of the murine anti-human BCMA monoclonal antibodies was performed according to methods as published in many documents in the art. Briefly, parental (murine antibody) constant domains were replaced with human constant domains. Human germline antibody sequences were selected according to the identity between the murine antibody and human antibody. The murine antibody M1 was humanized in the present disclosure.

On the basis of the typical structure of the VH/VL CDR of the obtained murine antibody, the sequences of heavy and light chain variable regions were aligned with the human antibody germline database to obtain human germline templates with high identity.

The CDR regions of the murine antibody M1 were grafted to the selected corresponding humanization templates. Then, based on the three-dimensional structure of the murine antibody, the embedded residues, the residues directly interacting with the CDR regions and the residues with significant influence on the conformation of VL and VH were subjected to back mutation, and chemically unstable amino acid residues in the CDR regions were optimized. After expression testing and comparison of the number of back mutations, the sequences of the humanized heavy chain variable region HCVRs were selected and designed, which are as follows:

```
HCVR1
                                              SEQ ID NO: 9
QVQLVQSGAEVKKPGASVKVSCKASGYSFSDYEMHWVRQAPGQGLEWMG

GIHPGSGGSAYNQKFKGRVTMTRDTSTSTVYMELSSLRSEDTAVYYCTR

LDYGYSWAWFPYWGQGTLVTVSA

HCVR2
                                             SEQ ID NO: 10
QVQLVQSGAEVKKPGASVKVSCKASGYSFSDYEMHWVRQAPGQGLEWIG

GIHPGSGGSAYNQKFKGRVTLTVDKSTSTAYMELSSLRSEDTAVYYCTR

LDYGYSWAWFPYWGQGTLVTVSA

HCVR3
                                             SEQ ID NO: 11
QVQLVQSGAEVKKPGASVKVSCKASGYSFSDYEMHWVRQAPGOGLEWIG

GIHPGSGGSAYNQKFKGKATLTVDKSTSTAYMELSSLRSEDTAVYYCTR

LDYGYSWAWFPYWGQGTLVTVSA
```

The sequences of the humanized light chain variable region LCVRs were selected and designed, which are as follows:

```
LCVR1
                                             SEQ ID NO: 12
EIVLTQSPATLSLSPGERATLSCSASSSVIYMNWYQQKPGQAPRLLIYG

ISNLASGIPARFSGSGSGTDFTLTISSLEPEDFAVYYCQQRSSYPLTFG

GGTKVEIK

LCVR2
                                             SEQ ID NO: 13
EIVLTQSPATLSLSPGERATLSCSASSSVIYMNWYQQKPGQSPKIWIYG

ISNLASGVPARFSGSGSGTDFTLTISSLEPEDFAVYYCQQRSSYPLTFG

GGTKVEIK

LCVR3
                                             SEQ ID NO: 14
EILLTQSPATLSLSPGERATLTCSASSSVIYMNWYQQKPGSSPKIWIYG

ISNLASGVPARFSGSGSGTSFTLTISSLEPEDFAVYYCQQRSSYPLTFG

GGTKVEIK
```

The designed heavy chain and light chain variable region sequences were linked to the human IgG1 heavy chain and light chain constant region sequences, respectively. Exemplary heavy chain and light chain constant region sequences are respectively as follows:

```
IgG1 C
                                             SEQ ID NO: 22
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV
```

-continued

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK

Ig kappa C
SEQ ID NO: 23
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

Exemplary heavy chain and light chain sequences obtained are as follows:

Ab1 HC
SEQ ID NO: 15
QVQLVQSGAEVKKPGASVKVSCKASGYSFSDYEMHWVRQAPGQGLEWMG

GIHPGSGGSAYNQKFKGRVTMTRDTSTSTVYMELSSLRSEDTAVYYCTR

LDYGYSWAWFPYWGQGTLVTVSAASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPGK

Ab2 HC
SEQ ID NO: 16
QVQLVQSGAEVKKPGASVKVSCKASGYSFSDYEMHWVRQAPGQGLEWIG

GIHPGSGGSAYNQKFKGRVTLTVDKSTSTAYMELSSLRSEDTAVYYCTR

LDYGYSWAWFPYWGQGTLVTVSAASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPGK

Ab3 HC
SEQ ID NO: 17
QVQLVQSGAEVKKPGASVKVSCKASGYSFSDYEMHWVRQAPGQGLEWIG

GIHPGSGGSAYNQKFKGKATLTVDKSTSTAYMELSSLRSEDTAVYYCTR

LDYGYSWAWFPYWGQGTLVTVSAASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

-continued

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPGK

Ab1 LC
SEQ ID NO: 18
EIVLTQSPATLSLSPGERATLSCSASSSVIYMNWYQQKPGQAPRLLIYG

ISNLASGIPARFSGSGSGTDFTLTISSLEPEDFAVYYCQQRSSYPLTFG

GGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

Ab2 LC
SEQ ID NO: 19
EIVLTQSPATLSLSPGERATLSCSASSSVIYMNWYQQKPGQSPKIWIYG

ISNLASGVPARFSGSGSGTDFTLTISSLEPEDFAVYYCQQRSSYPLTFG

GGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

Ab3 LC
SEQ ID NO: 20
EILLTQSPATLSLSPGERATLTCSASSSVIYMNWYQQKPGSSPKIWIYG

ISNLASGVPARFSGSGSGTSFTLTISSLEPEDFAVYYCQQRSSYPLTFG

GGTKVEIKRTVAAPSVFIFPPSDEQLKSGTASVVCLLNNFYPREAKVQW

KVDNALQSGNSQESVTEQDSKDSTYSLSSTLILSKADYEKHKVYACEVT

HQGLSSPVTKSFNRGEC

TABLE 5

Antibodies and SEQ ID NOs, of heavy chain, light chain and variable regions thereof

| Humanized antibody NO. | Heavy chain/ light chain NO. | Heavy chain/light chain variable region NO. |
|---|---|---|
| Ab1 | SEQ ID NO: 15 | SEQ ID NO: 9 |
| | SEQ ID NO: 18 | SEQ ID NO: 12 |
| Ab2 | SEQ ID NO: 16 | SEQ ID NO: 10 |
| | SEQ ID NO: 19 | SEQ ID NO: 13 |
| Ab3 | SEQ ID NO: 17 | SEQ ID NO: 11 |
| | SEQ ID NO: 20 | SEQ ID NO: 14 |

cDNA fragments were synthesized according to the amino acid sequences of the light chain and heavy chain of each humanized antibody above, and inserted into the pcDNA3.1 expression vector (Life Technologies Cat. No. V790-20). The expression vector was used along with the transfection reagent PEI (Polysciences, Inc. Cat. No. 23966) at a ratio of 1:2 to transfect HEK293 cells (Life Technologies Cat. No. 11625019). The cells were incubated in a $CO_2$ incubator for 4-5 days. The cell culture fluid was collected, centrifuged and filtered. Then the samples were loaded on the antibody purification affinity column. The column was washed with phosphate buffer. The samples were eluted with glycine-hydrochloric acid buffer (pH 2.7, 0.1M Gly-HCl), neutralized with 1M Tris hydrochloric acid pH 9.0, and dialyzed against phosphate buffer to obtain the humanized antibody proteins of the present disclosure.

Example 6: In Vitro Binding Affinity and Kinetic Assay

The affinity ($EC_{50}$) of each humanized antibody to human BCMA antigen was determined by using the in vitro indirect ELISA binding assay according to Example 4 (1), and is as shown in table below:

TABLE 6

| Affinity of each humanized antibody to human BCMA antigen ($EC_{50}$) | | |
|---|---|---|
| Humanized antibody | Antigen | Affinity $EC_{50}$ (nM) |
| Ab1 | BCMA-His | 0.022 |
| Ab2 | | 0.033 |
| Ab3 | | 0.034 |

The affinity ($EC_{50}$) of each humanized antibody to NCI-H929 tumor cells was determined by using the in vitro cell binding assay according to Example 4 (2), and is as shown in Table 7 below:

TABLE 7

| Affinity ($EC_{50}$) of each humanized antibody to NCI-H929 tumor cells | | |
|---|---|---|
| Humanized antibody | Cell | Affinity EC50 (nM) |
| Ab1 | NCI-H929 | 4.6 |
| Ab2 | | 3.5 |
| Ab3 | | 3.9 |

Example 7: Endocytosis of the Antibodies

NCI-H929 was used for evaluating whether the antibodies of the present disclosure could be endocytosed into cells along with human BCMA after binding to BCMA. NCI-H929 cells were digested with trypsin (after washed once with PBS at 37 °C for about 2 min), collected and re-suspended in pre-cooled FACS buffer. The cell concentration was adjusted to $1\times10^6$ cells/mL. 1 mL of cell suspension was added to an EP tube, centrifuged at 1500 rpm for 5 minutes, and the supernatant was removed. 1 mL of the prepared antibody to be tested was added to re-suspend the cells, and the final concentration of the antibody was 20 μg/ml. The cells were incubated in a shaker at 4 °C for 1 hour, centrifuged (4 °C, 1500 rpm×5 min), and the supernatant was discarded. The cells were washed twice with FACS buffer and the supernatant was removed. 100 μL of fluorescent secondary antibody working solution was added to each tube to re-suspend the cells. The cells were incubated in a shaker at 4 °C for 30 min, centrifuged (4 °C, 1500 rpm×5 min), and the supernatant was discarded. The cells were washed twice with FACS buffer and the supernatant was removed. 1.0 mL of pre-warmed NCI-H929 cell complete medium was added to each tube to re-suspend the cells and mixed thoroughly. The cell suspension was aliquoted into 4 tubes, 200 μL per tube, respectively as 0 min group, blank group, 30 min group and 2 h group. The 0 min and blank groups were placed on ice, while the rest groups were placed in an incubator at 37 °C for endocytosis for 30 min and 2 h respectively. At the corresponding time point, the EP tube was taken out and placed on ice to pre-cooled for 5 min. All treatment groups were centrifuged (4 °C, 1500 rpm×5 min) and the supernatant was discarded. The cells were washed once with FACS buffer and the supernatant was removed. 250 μL strip buffer was added to EP tubes of all treatment groups except the 0 min group. The cells were incubated at room temperature for 8 min, centrifuged (4 °C, 1500 rpm×5 min) and the supernatant was discarded. The cells were washed twice with FACS buffer and the supernatant was removed. All treatment groups were added with 100 μL fixing solution, placed at 4 °C for more than 30 min for immunostaining, and detected by the flow cytometer DxFlex. Percentage of BCMA antibody endocytosis=(fluorescence intensity value at each time point−average fluorescence intensity value of the 0 min group)/average fluorescence intensity value of the 0 min group. The results are shown in table below:

TABLE 8

| Endocytosis ($EC_{50}$) of antibodies into NCI-H929 tumor cells | | | |
|---|---|---|---|
| Humanized | | Endocytosis efficiency % | |
| antibody | Cell | 0.5 hour | 2 hours |
| Ab1 | NCI-H929 | 36.6 | 49.5 |
| Ab2 | | 36.7 | 48 |
| Ab3 | | 35.5 | 45.7 |

Example 8: Preparation of Antibody Drug Conjugates

Preparation of ADC2:

(ADC2)

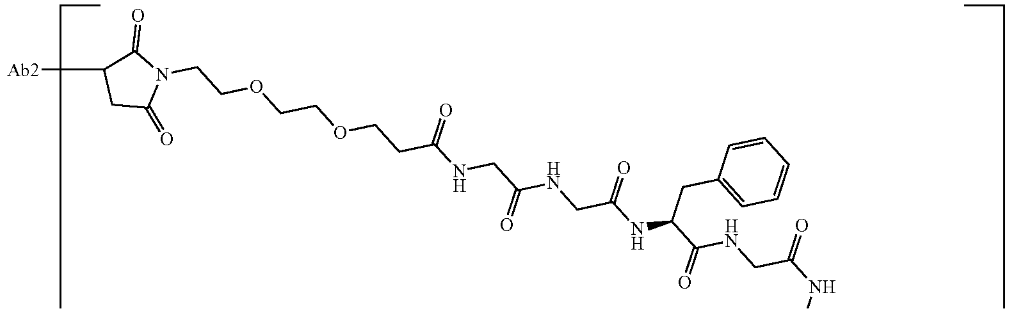

-continued

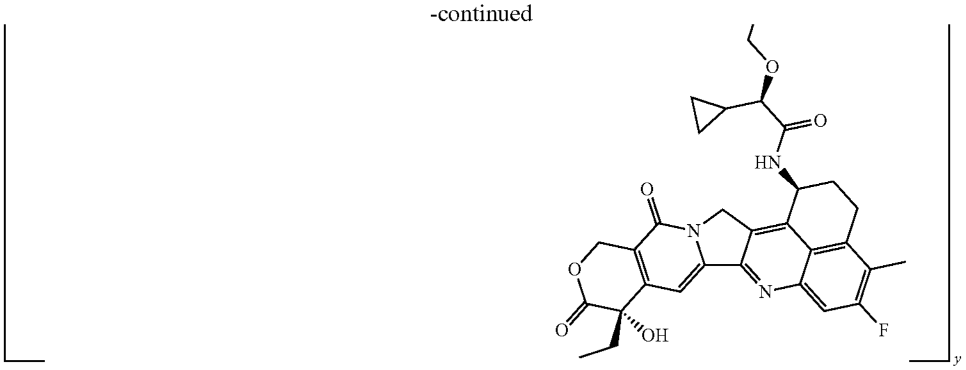

A formulated aqueous solution of tris(2-carboxyethyl) phosphine (10 mM, 0.347 mL, 3.47 μmol) was added to a PBS-buffered aqueous solution of antibody Ab2 (0.05 M PBS-buffered aqueous solution with pH=6.5; 7.3 ml, 13.8 mg/ml, 0.681 μmol) at 37 °C. The reaction solution was placed in a water bath shaker, and shaked at 37 °C for 3 hours before stopping the reaction. The reaction solution was cooled to 25 °C in a water bath, and diluted to 14.0 ml. 3.3 ml of the solution was taken for the next reaction.

Compound D (3.0 mg, 3.72 μmol) was dissolved in 0.15 ml DMSO, and then added to the above 3.3 ml solution. The reaction solution was placed in a water bath shaker, and shaked at 25 °C for 3 hours before stopping the reaction. The reaction solution was desalted and purified with a Sephadex G25 gel column (elution phase: 0.05M PBS-buffered aqueous solution with pH=6.5, containing 0.001M EDTA) to obtain the PBS-buffered solution of the exemplary product ADC2 as shown in formula Ab2 antibody conjugate (1.35 mg/ml, 13 ml). The solution was frozen at 4 °C.

The average value y was determined by the ultraviolet method. Cuvettes filled with sodium succinate buffer were respectively placed in the reference absorption cell and the sample determination absorption cell, and after deducting the solvent blank, the cuvettes filled with the test solution were placed in the sample determination absorption cell. The absorbance at 280 nm and 370 nm was measured.

Data Processing:

The antibody content $C_{Ab}$ was determined by establishing a standard curve and measuring the absorption at the wavelength of 280 nm. The small molecule content $C_{Drug}$ was determined by measuring the absorption at the wavelength of 370 nm.

Average value of drug load $y=C_{Drug}/C_{Ab}$.

As for the exemplary product ADC2, y was determined to be 4 by the above method. Samples of ADC2 (y=4) were obtained by UV-HPLC purification.

Example 9: The Killing Activity of Antibody Drug Conjugates on Tumor Cells

In order to test the killing effect of the antibody drug conjugates of the present disclosure on tumor cells, The BCMA high expression cell line NCI-H929 cells (ATCC deposit number CRL-9068) were used for evaluation. NCI-H929 cells were collected, centrifuged and counted. The cell density was adjusted to $1\times10^5$ cells/mL with complete medium, and the cells were plated in 60 wells of a white 96-well plate at 100 μL per well with a cell number of 10,000 cells/well. The rest peripheral wells were added with 100 μL DPBS per well. The cell plate was placed in a 37 °C, 5% $CO_2$ incubator and cultured overnight. On the second day of the experiment, the antibody-drug conjugate working solution was prepared with complete medium in a 96-well V-bottom plate, starting from a concentration of 133 μM (5-fold dilution and 9 concentrations). After completion of the preparation, the solution was added to a white 96-well plate at 80 μL per well in duplicates. The cell plate was placed in a 37 °C, 5% $CO_2$ incubator and the culture lasted for 72 hours. On the fifth day of the experiment, the plate was detected and read. The cell culture plate was taken out. 90 μL CellTiter-Glo® solution (Promega, Cat #: G7573) was added to each well after equilibrating to room temperature. The mixture was shaken and mixed, placed in dark and let stand for 10 minutes, and then detected by using the luminescence program of the microplate reader. The $IC_{50}$ values were calculated using GraphPad Prims software. The ADC (y=4) of negative antibody IgG1 conjugated with compound D was used as negative control. The experimental results are shown in the table below:

TABLE 9

Evaluation of the killing activity of antibody drug conjugates on tumor cells

| Antibody drug conjugate | Killing Effect ($IC_{50}$ nM) NCI-H929 |
|---|---|
| ADC2 (y = 4) | 0.76 |
| IgG1 iso ADC (y = 4) | >133 |

The experimental results showed that ADC2 (y=4) had good killing activity on tumor cells in vitro.

Example 10: Tumor Killing Activity of Antibody Drug Conjugates

In order to further investigate the inhibition effect of the antibody drug conjugates on the proliferation of tumors formed in vivo, the anti-tumor effect of the antibody drug conjugates of the present disclosure was evaluated after formation of transplanted tumors with NCI-H929 (ATCC deposit number CRL-9068) cell line in mice. $10\times10^6$ NCI-H929 cells were injected subcutaneously into the back of 6-8 week-old immunodeficient nude mice (NOD-SCID). After 14 days, intravenous injection of the antibody drug conjugates via caudal vein were performed, at a frequency of once/week, continuous administration for two weeks at a dose of 3 mg/kg. Human IgG1 isotype control protein was used as the control at a dose of 3 mg/kg. There were 5 mice in each group of the control group or the administration group. The tumor inhibition rate was calculated by measuring the tumor volume, as follows:

Tumor inhibition rate TGI %=100%−(tumor volume of the administration group on day 14−tumor volume of the administration group on day 0)/

(tumor volume of the control group on day 14−tumor volume of the control group on day 0).

The experimental results are shown in the table below:

TABLE 10

| Killing activity of antibody drug conjugates on tumors | |
|---|---|
| Group | Tumor inhibition rate (%) |
| IgG1 iso ADC (y = 4), 3 mpk | — |
| ADC2 (y = 4), 3 mpk | 164.67 |

The experimental results showed that the antibody drug conjugate ADC2 (y=4) showed good tumor inhibition effect in vivo.

What is claimed is:
1. A compound of formula (D), wherein the structure of the compound is:
(D)
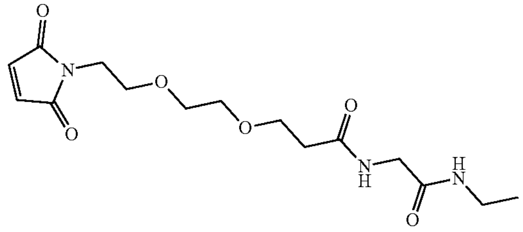
-continued
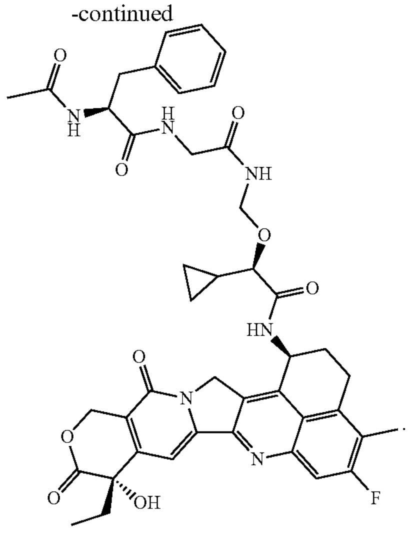
2. An antibody drug conjugate represented by formula (II) or a tautomer or mesomer thereof or a pharmaceutically acceptable salt or solvate thereof, wherein an antibody is conjugated to the compound of formula (D) according to claim 1,
(II)
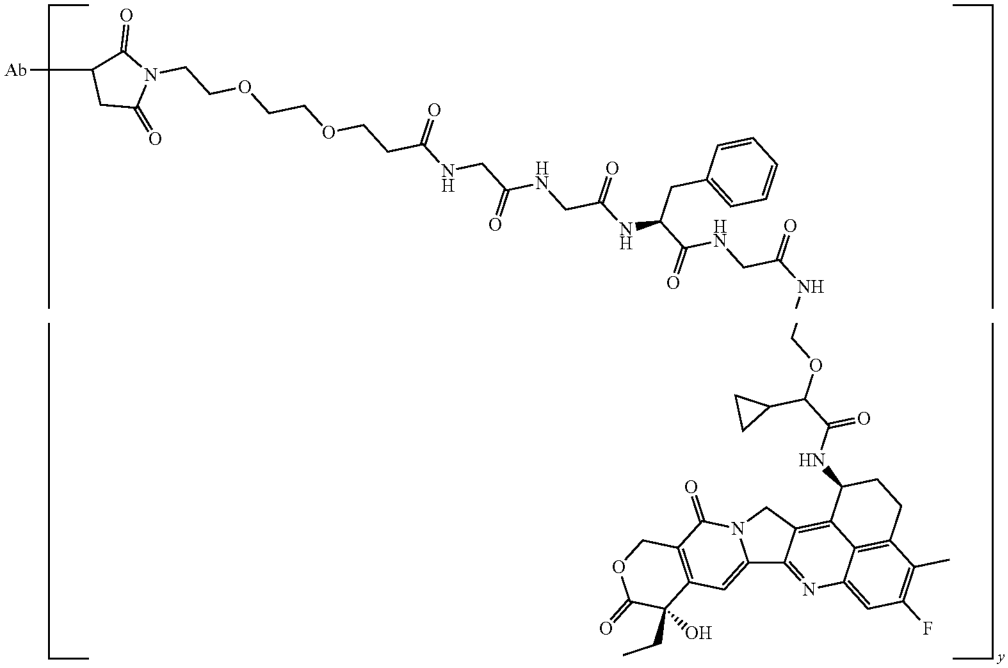

wherein: y is 1-8 and Ab is an antibody or an antigen-binding fragment.

3. The antibody drug conjugate or the pharmaceutically acceptable salt or solvate thereof according to claim 2, wherein the Ab is an anti-BCMA antibody or antigen-binding fragment comprising a heavy chain variable region and a light chain variable region, wherein the heavy chain variable region comprises an HCDR1, an HCDR2 and an HCDR3 set forth in SEQ ID NO: 3, SEQ ID NO: 4 and SEQ ID NO: 5, respectively, and the light chain variable region comprises an LCDR1, an LCDR2 and an LCDR3 set forth in SEQ ID NO: 6, SEQ ID NO: 7 and SEQ ID NO: 8, respectively, and wherein y is 4-8.

4. The antibody drug conjugate or the pharmaceutically acceptable salt or solvate thereof according to claim 3, wherein y is 4, 6, or 8.

5. The antibody drug conjugate or the pharmaceutically acceptable salt or solvate thereof according to claim 4, wherein the anti-BCMA antibody or the antigen-binding fragment thereof is a murine antibody, a chimeric antibody, or a humanized antibody.

6. The antibody drug conjugate or the pharmaceutically acceptable salt or solvate thereof according to claim 5, wherein the anti-BCMA antibody or the antigen-binding fragment thereof further comprises the heavy chain constant region as shown in SEQ ID NO:22, and the light chain constant region as shown in SEQ ID NO: 23.

7. The antibody drug conjugate or the pharmaceutically acceptable salt or solvate thereof according to claim 5, wherein:

the anti-BCMA antibody or the antigen-binding fragment thereof comprises a heavy chain variable region as shown in SEQ ID NO: 10 and a light chain variable region as shown in SEQ ID NO: 13; or the anti-BCMA antibody or the antigen-binding fragment thereof comprises a heavy chain variable region as shown in SEQ ID NO: 9 and a light chain variable region as shown in SEQ ID NO: 12; or the anti-BCMA antibody or the antigen-binding fragment thereof comprises a heavy chain variable region as shown in SEQ ID NO: 11 and a light chain variable region as shown in SEQ ID NO: 14.

8. The antibody drug conjugate or the pharmaceutically acceptable salt or solvate thereof according to claim 4, wherein:

the anti-BCMA antibody or the antigen-binding fragment thereof comprises a heavy chain as shown in SEQ ID NO: 16, SEQ ID NO: 15 or SEQ ID NO: 17, or a heavy chain having at least 80%, 85%, 90%, 95% or 99% identity with the same;

and/or the anti-BCMA antibody or the antigen-binding fragment thereof comprises a light chain as shown in SEQ ID NO: 19, SEQ ID NO: 18 or SEQ ID NO: 20, or a light chain having at least 80%, 85%, 90%, 95% or 99% identity with the same.

9. The antibody drug conjugate or the pharmaceutically acceptable salt or solvate thereof according to claim 8, wherein:

the anti-BCMA antibody comprises a heavy chain as shown in SEQ ID NO: 16 and a light chain as shown in SEQ ID NO: 19, or the anti-BCMA antibody comprises a heavy chain as shown in SEQ ID NO: 15 and a light chain as shown in SEQ ID NO: 18, or the anti-BCMA antibody comprises a heavy chain as shown in SEQ ID NO: 17 and a light chain as shown in SEQ ID NO: 20.

10. The antibody drug conjugate or the pharmaceutically acceptable salt or solvate thereof according to claim 2, wherein the antibody drug conjugate or the pharmaceutically acceptable salt or solvate is selected from the group consisting of the following structures:

(ADC1)

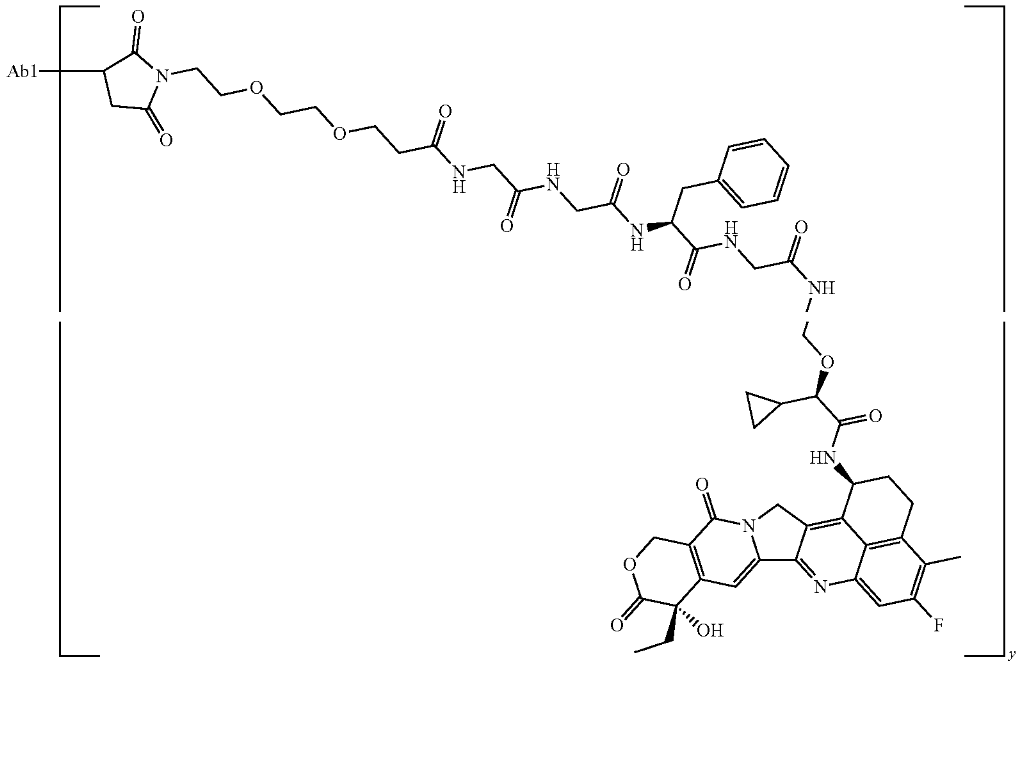

-continued
(ADC2)
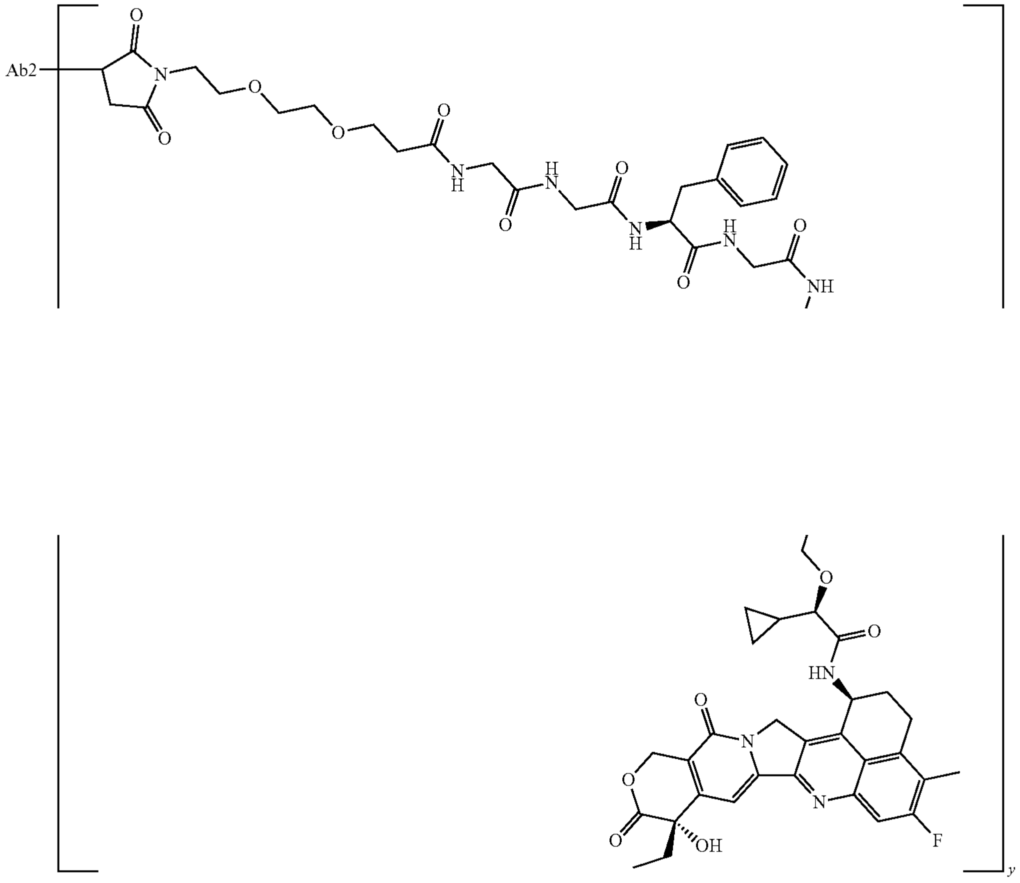
(ADC3)
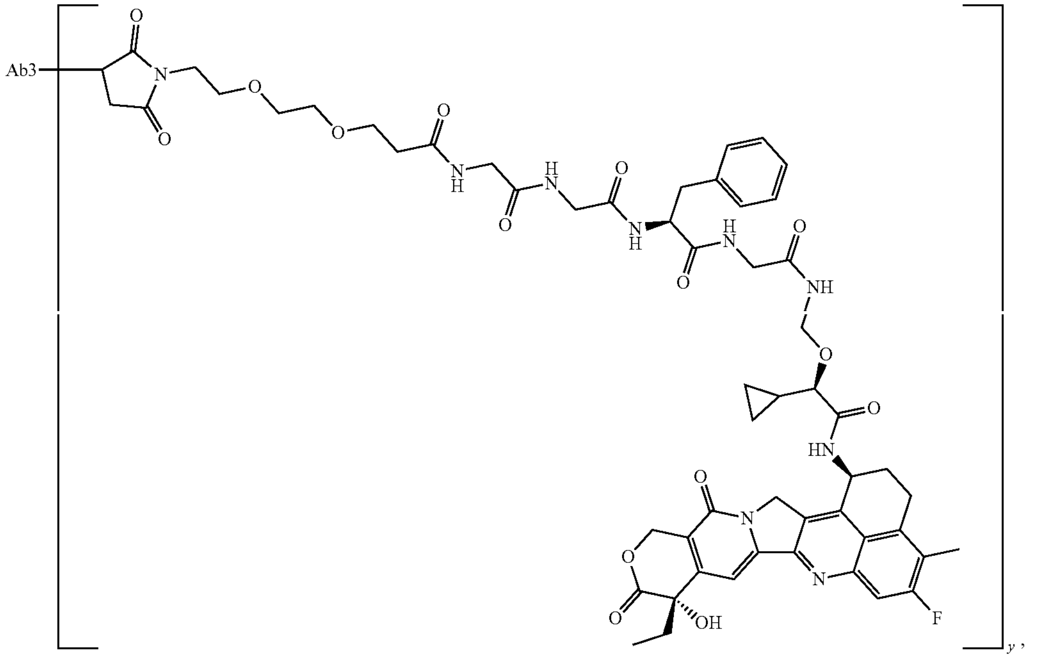
wherein y is as defined in claim 2.

11. A method for preparing the antibody drug conjugate of formula (II) or the pharmaceutically acceptable salt or solvate thereof, which comprises the following steps:

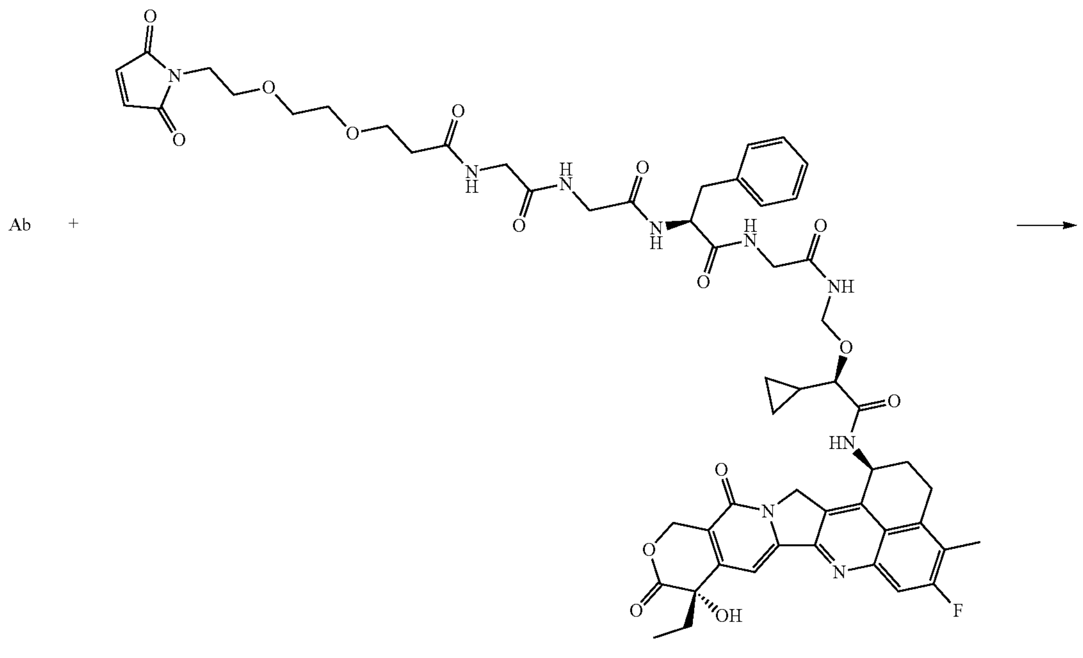

(D)

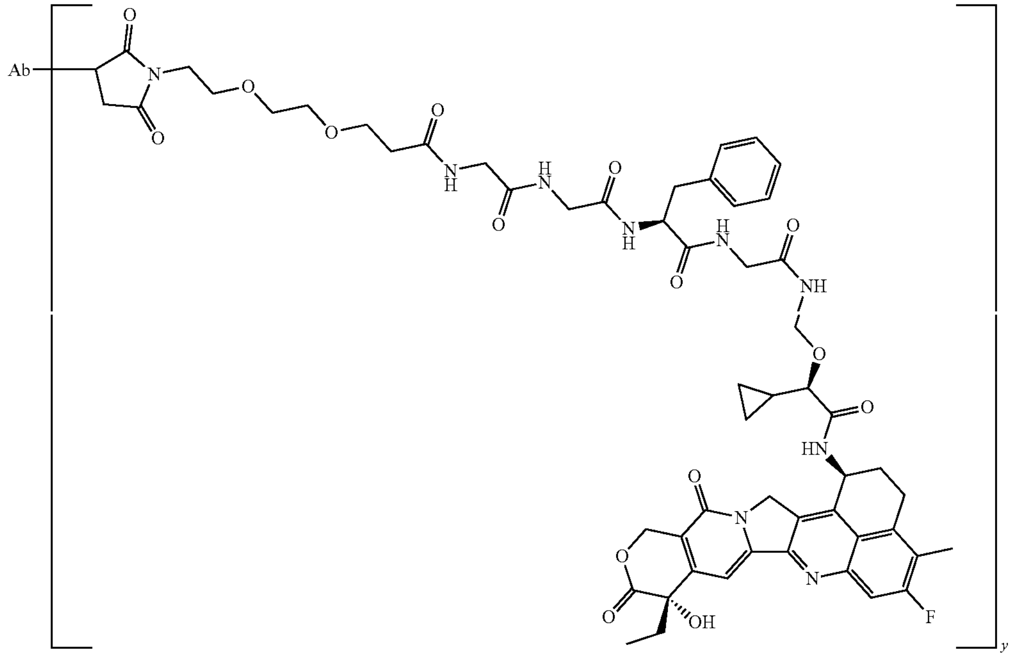

(II)

after Ab is reduced, it is subjected to coupling reaction with general formula (D) to obtain the compound of formula (II); wherein: Ab and y are as defined in claim 2.

12. A pharmaceutical composition comprising the antibody drug conjugate according to claim 2, or the pharmaceutically acceptable salt or solvate thereof, and one or more pharmaceutically acceptable excipients, diluents or carriers.

13. A method of treating a BCMA-mediated disease or condition, wherein the BCMA-mediated disease or condition is a cancer expressing BCMA or an autoimmune disease expressing BCMA, comprising administering to a subject in need thereof a therapeutically effective amount of the antibody drug conjugate or the pharmaceutically acceptable salt or solvate thereof according to claim 3, or the pharmaceutical composition according to claim 12.

14. The method according to claim 13, wherein the cancer is lymphoma, leukemia or myeloma.

15. The method according to claim 13, wherein the autoimmune disease is selected from the group consisting of lupus erythematosus, IgA nephropathy and rheumatic arthritis.

* * * * *